(12) United States Patent
Thurston

(10) Patent No.: US 10,442,864 B2
(45) Date of Patent: *Oct. 15, 2019

(54) ANTI-TIE2 ANTIBODIES AND USES THEREOF

(71) Applicant: Regeneron Pharmaceuticals, Inc., Tarrytown, NY (US)

(72) Inventor: Gavin Thurston, Briarcliff Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,399

(22) Filed: Jun. 13, 2018

(65) Prior Publication Data

US 2018/0291105 A1    Oct. 11, 2018

Related U.S. Application Data

(60) Continuation of application No. 15/373,903, filed on Dec. 9, 2016, now Pat. No. 10,023,641, which is a continuation of application No. 14/671,494, filed on Mar. 27, 2015, now Pat. No. 9,546,218, which is a division of application No. 13/586,911, filed on Aug. 16, 2012, now Pat. No. 9,017,670.

(60) Provisional application No. 61/674,405, filed on Jul. 23, 2012, provisional application No. 61/587,213, filed on Jan. 17, 2012, provisional application No. 61/525,308, filed on Aug. 19, 2011.

(51) Int. Cl.
```
C07K 16/18      (2006.01)
C07K 16/28      (2006.01)
A61K 39/395     (2006.01)
C07K 16/40      (2006.01)
C07K 14/705     (2006.01)
C07K 14/71      (2006.01)
A61K 39/00      (2006.01)
```

(52) U.S. Cl.
CPC ...... *C07K 16/2863* (2013.01); *A61K 39/3955* (2013.01); *A61K 39/39533* (2013.01); *C07K 16/40* (2013.01); *A61K 39/395* (2013.01); *A61K 2039/505* (2013.01); *C07K 14/705* (2013.01); *C07K 14/71* (2013.01); *C07K 16/28* (2013.01); *C07K 16/2896* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
CPC .......... A61K 2300/00; A61K 2039/505; A61K 39/395; A61K 39/39533; C07K 16/2863; C07K 16/2866; C07K 2317/56; C07K 2317/76; C07K 2316/96; C07K 16/40; C07K 16/28; C07K 14/705
See application file for complete search history.

(56) References Cited

U.S. PATENT DOCUMENTS

| | | |
|---|---|---|
| 5,447,860 A | 9/1995 | Ziegler |
| 5,681,714 A | 10/1997 | Breitman et al. |
| 5,998,187 A | 12/1999 | Breitman et al. |
| 6,365,154 B1 | 4/2002 | Holmes et al. |
| 6,376,653 B1 | 4/2002 | Holmes et al. |
| 6,413,932 B1 | 7/2002 | Cerretti et al. |
| 6,521,424 B2 | 2/2003 | Cerretti et al. |
| 7,067,475 B2 | 6/2006 | Cerretti et al. |
| 7,485,297 B2 | 2/2009 | Wood et al. |
| 8,980,268 B2 | 3/2015 | Lowy et al. |
| 9,017,670 B2 | 4/2015 | Thurston |
| 9,546,218 B2 | 1/2017 | Thurston |
| 10,023,641 B2 | 7/2018 | Thurston |
| 2003/0040463 A1 | 2/2003 | Wiegand et al. |
| 2004/0101920 A1 | 5/2004 | Radziejewski |
| 2004/0147449 A1 | 7/2004 | Siemeister et al. |
| 2006/0057138 A1 | 3/2006 | Wood et al. |
| 2017/0088622 A1 | 3/2017 | Thurston et al. |

FOREIGN PATENT DOCUMENTS

| | | |
|---|---|---|
| EP | 1117692 B1 | 11/2006 |
| EP | 1880993 A1 | 1/2008 |
| EP | 1187918 B9 | 1/2009 |
| WO | 95/013387 A1 | 5/1995 |
| WO | 95/021866 A1 | 8/1995 |
| WO | 00/018437 A1 | 4/2000 |
| WO | 00/018804 A1 | 4/2000 |
| WO | 00/075323 A1 | 12/2000 |
| WO | 06/005361 A1 | 1/2006 |
| WO | 06/020706 A2 | 2/2006 |
| WO | 08/049227 A1 | 5/2008 |
| WO | 10/011242 A2 | 1/2010 |
| WO | 13/028442 A1 | 2/2013 |

OTHER PUBLICATIONS

"Anti-Tie2 Antibody (ab10349)," Abcam, 2 pages, (2012). [Retrieved from the Internet on Nov. 14, 2012: <URL: http//www.abcam.com/TIE2-antibody-ab10349.html>]. [Author unknown].

(Continued)

*Primary Examiner* — Bridget E Bunner
(74) *Attorney, Agent, or Firm* — Schwabe, Williamson & Wyatt PC; Gabe Amodeo

(57) ABSTRACT

The present invention provides antibodies that bind to Tie2 and methods of using same. According to certain embodiments of the invention, the antibodies are fully human antibodies that bind to human Tie2 and block the interaction between Tie2 and one or more Tie2 ligands such as angiopoietin 1 (Ang1), angiopoietin 2 (Ang2), angiopoietin 3 (Ang3) and/or angiopoietin 4 (Ang4). The antibodies of the invention are useful, inter alia, for the treatment of diseases and disorders associated with one or more Tie2 biological activities including angiogenesis.

7 Claims, 7 Drawing Sheets

Specification includes a Sequence Listing.

(56) References Cited

OTHER PUBLICATIONS

"Human Tie-2 antibody, Antigen Affinity-Purified Polyclonal Goat IgG," R&D Systems, Catalog No. AF313, 1 page, (2012). [Retrieved from the Internet on Nov. 14, 2012: <URL: http://www.rndsystems.com/pdf/af313.pdf>]. [Author unknown].
"Lyme Disease", <http://www.aldf.com/lyme-disease/: downloaded Jun. 29, 2018; 23 pages.
Adler et al., "Blockade or angiopoietin-2 or Tie2 is equally effective at inhibiting tumor growth and reducing tumor vessel density in most human tumor xenograft models," [abstract], In: Proceedings of the 105th AACR Annual Meeting, Cancer Res, 74(19 Suppl):Abstract nr 4492, doi:10.1158/1538-7445.AM2014-4492, (2014).
Barton et al., "Crystal structures of the Tie2 receptor ectodomain and angiopoietin-2-Tie2 complex," Nature Structural and Molecular Biology, 13(6):524-532, (2006).
Barton et al., "Structure of the Angiopoietin-2 Receptor Binding Domain and Identification of Surfaces Involved in Tie2 Recognition," Structure, 13(5):825-832, (2005).
Currie et al., "Expression of the Angiopoietins and their Receptor Tie2 in Human Renal Clear Cell Carcinomas; Regulation by the von Hippel-Lindau Gene and Hypoxia," Journal of Pathology, vol. 198:502-510, (2002).
D'Ettorre et al., "HIV-Associated Immune Activation: From the Bench to Bedside," AIDS Research and Human Retroviruses, vol. 27 (No. 4):355-364, (2011).
Dumont et al., "tek, a novel tyrosine kinase gene located on mouse chromosome 4, is expressed in endothelial cells and their presumptive precursors," Oncogene, 7(8):1471-1480, (1992).
Eklund et al., "Tie receptors and their angiopoietin ligands are context-dependent regulators of vascular remodeling," Experimental Cell Research, 312:630-641, (2005).
Feistritzer et al., "Expression and function of the angiopoietin receptor Tie-2 in human eosinophils," Journal of Allergy and Clinical Immunology, 114(5):1077-1084, (2004).
Fiedler et al. "Angiopoietin-1 and Angiopoietin-2 share the same binding domains in the Tie-2 receptor involving the first Ig-like loop and the epidermal growth factor-like repeats," J Biol Chem, 278(3):1721-1727, (2003).
Han et al., "Amelioration of sepsis by TIE2 activation-induced vascular protection," Science Translation Medicine, vol. 8 (Issue 335):12 pages, Apr. 20, 2016. [Retrieved from the Internet Jun. 29, 2018: <URL: http://stm.sciencemag.org/>].
Hansen et al., "Effects of angiopoietins-1 and -2 on the receptor tyrosine kinase Tie2 are differentially regulated at the endothelial cell surface"; Elsevier, Cellular Signalling 22 (2010) 527-532.
Huang et al., "Targeting the ANGPT—TIE2 Pathway in Malignancy," Nature Reviews, vol. 10:575-585, (Aug. 2010).
Janeway, Jr. et al., "Immuno Biology: The Immune System in Health and Disease", 3rd ed., (1997), New York: current Biology Limited, p. 9:37-9:38.
Kosacka et al., "Angiopoietin-1 promotes neurite outgrowth from dorsal root ganglion cells positive for Tie-2 receptor," Cell and Tissue Research, 320:11-19, (2005).
Liu et al., "Tie2: A Journey from Normal Angiogenesis to Cancer and Beyond," Histology and Histopathology, vol. 23:773-780, (2008). <URL: http://www.hh.um.es>].

MacDonald et al., "Structure of the extracellular domain of Tie receptor tyrosine kinases and localization of the angiopoietin-binding epitope," J Biol Chem, 281:28408-28414, (2006).
Maisonpierre et al., "Angiopoietin-2, a natural antagonist for Tie2 that disrupts in vivo angiogenesis," Science, 277(5322):55-60, (1997).
Mitsutake et al., "Tie-2 and Angiopoietin-1 Expression in Human Thyroid Tumors," Thyroid, vol. 12, No. 2: 95-99; (2002).
Reikvam et al., "Targeting the angiopoietin (Ang)/Tie-2 pathway in the crosstalk between acute myeloid leukemia and endothelial cells: studies of Tie-2 blocking antibodies, exogenous Ang-2 and inhibition of constitutive agonistic Ang-1 release," Expert Opinion on Investigational Drugs, 19(2):169-183, (2010).
Sato et al., "tie-1 and tie-2 define another class of putative receptor tyrosine kinase genes expressed in early embryonic vascular system," Proc Natl Acad Sci (USA), 90(20):9355-9358, (1993).
Shim et al., "Angiopoietin: A TIE(d) Balance in Tumor Angiogenesis," Mol Cancer Res, 5(7):655-665, (2007).
Sugiyama et al., "The Tie2-agonist Vasculotide rescues mice from influenza virus infection," Scientific Report, vol. 5(No. 11030):10 pages, (2015).
Thurston, "Role of angiopoietins and Tie receptor tyrosine kinases in angiogenesis and lymphangiogenesis," Cell Tissue Res, 314:61-68, (2003).
U.S. Appl. No. 13/586,911, Non-Final Office Action dated Feb. 19, 2014.
U.S. Appl. No. 13/586,911, Non-Final Office Action dated Jul. 31, 2014.
U.S. Appl. No. 13/586,911, Notice of Allowance dated Jan. 2, 2015.
U.S. Appl. No. 13/586,911, Requirement for Restriction/Election dated Dec. 3, 2013.
U.S. Appl. No. 14/671,494, Non-Final Office Action dated Mar. 21, 2016.
U.S. Appl. No. 14/671,494, Notice of Allowance dated Sep. 9, 2016.
U.S. Appl. No. 15/373,903, Non-Final Office Action dated Oct. 19, 2017.
U.S. Appl. No. 15/373,903, Notice of Allowance dated Mar. 13, 2018.
U.S. Appl. No. 15/445,563, Non-Final Office Action dated Jul. 9, 2018.
U.S. Appl. No. 15/445,563, Requirement for Restriction/Election dated Feb. 2, 2018.
WIPO Application No. PCT/US2012/051038, PCT International Preliminary Report on Patentability dated Mar. 6, 2014.
WIPO Application No. PCT/US2012/051038, PCT International Search Report dated May 12, 2012.
WIPO Application No. PCT/US2012/051038, PCT Written Opinion of the International Searching Authority dated May 12, 2012.
Ziegler et al., "Molecular cloning and characterization of a novel receptor protein tyrosine kinase from human placenta," Oncogene, 8(3):663-670, (1993).
U.S. Appl. No. 15/445,563, Notice of Allowance dated Jan. 23, 2019.
Hansbury et al., "Production and characterization of a Tie2 agonist monoclonal antibody," Angiogenesis, vol. 4:29-36, (2001).
Hwang et al., "Stimulation of angiogenesis and survival of endothelial cells by human monoclonal Tie2 receptor antibody," Biomaterials, vol. 51:119-128, (2015).
Yuan et al., "Activation of the orphan endothelial receptor Tie1 modifies Tie2-mediated intracellular signaling and cell survival," FASEB Journal, vol. 21:3171-3183, (2007).

ANTI-TIE2 ANTIBODIES AND USES THEREOF

CROSS-REFERENCE TO RELATED APPLICATIONS

This application is a continuation of U.S. application Ser. No. 15/373,903, filed Dec. 9, 2016, now U.S. Pat. No. 10,023,641, which is a continuation of U.S. application Ser. No. 14/671,494, filed Mar. 27, 2015, now U.S. Pat. No. 9,546,218, which is a division of U.S. application Ser. No. 13/586,911, filed Aug. 16, 2012, now U.S. Pat. No. 9,017,670, which claims the benefit under 35 U.S.C. § 119(e) of U.S. Provisional Application Nos. 61/525,308, filed on Aug. 19, 2011; 61/587,213, filed on Jan. 17, 2012; and 61/674,405, filed on Jul. 23, 2012, the disclosures of which are herein incorporated by reference in their entireties.

SEQUENCE LISTING

This application incorporates by reference the Sequence Listing submitted in Computer Readable Form as file 7100US05-Sequence.txt, created on Jun. 13, 2018 and containing 95,478 bytes.

FIELD OF THE INVENTION

The present invention relates to antibodies, and antigen-binding fragments thereof, which are specific for human Tie2.

BACKGROUND

Angiogenesis is the biological process whereby new blood vessels are formed. Aberrant angiogenesis is associated with several disease conditions including, e.g., proliferative retinopathies, rheumatoid arthritis and psoriasis. In addition, it is well established that angiogenesis is critical for tumor growth and maintenance. Tie2 is a single transmembrane tyrosine kinase receptor that has been localized to the endothelial cells of forming blood vessels and has been shown to play a role in angiogenesis. Tie2 ligands include the angiopoietins (e.g., Ang1, Ang2, Ang3 and Ang4). Blocking the interaction between Tie2 and one or more of its ligands is expected to have beneficial therapeutic effects in settings where it is advantageous to limit or block angiogenesis.

Antibodies to Tie2 are mentioned, e.g., in U.S. Pat. Nos. 6,365,154 and 6,376,653. Nonetheless, there remains a need in the art for novel molecules capable of binding to Tie2, especially anti-Tie2 antibodies that can block the interaction of Tie2 with one or more Tie2 ligands such as Ang2. Such molecules would be useful for various therapeutic and diagnostic purposes.

BRIEF SUMMARY OF THE INVENTION

The present invention provides antibodies that bind human Tie2. The antibodies of the invention are useful, inter alia, for inhibiting Tie2-mediated signaling and for treating diseases and disorders caused by or related to Tie2 activity and/or signaling. According to certain embodiments, the antibodies of the invention block the interaction between Tie2 and one or more Tie2 ligands such as Ang1, Ang2, Ang3, and/or Ang4.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

The present invention provides anti-Tie2 antibodies that have substantially the same binding characteristics as any of the exemplary anti-Tie2 antibodies described herein. The present invention includes cell lines that produce the anti-Tie2 antibodies described herein. As non-limiting examples, cell lines which produce the exemplary antibodies H1M2055N and H2aM2760N were deposited under terms in accordance with the Budapest Treaty with the American Type Culture Collection (ATCC), 10801 University Blvd., Manassas, Va. 20110-2209 on Dec. 2, 2011. The deposited cell lines have been assigned the following accession numbers: PTA-12295 (H1M2055N) and PTA-12296 (H2aM2760N).

The present invention provides nucleic acid molecules encoding the exemplary anti-Tie2 antibodies described herein. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes antibodies and antigen-binding fragments thereof comprising the heavy and light chain CDR amino acid sequences (HCDR1, HCDR2, HCDR3, LCDR1, LCDR2 and LCDR3) found within any of the exemplary anti-Tie2 antibodies described herein, including the antibodies produced by the deposited cell lines PTA-12295 and PTA-12296. The present invention also includes antibodies and antigen-binding fragments thereof comprising the heavy and light chain variable domain amino acid sequences (HCVR and LCVR) found within any of the exemplary anti-Tie2 antibodies described herein, including the antibodies produced by the deposited cell lines PTA-12295 and PTA-12296.

The present invention includes any of the exemplary anti-Tie2 antibodies described herein having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides pharmaceutical compositions comprising an anti-Tie2 antibody as described herein and a pharmaceutically acceptable carrier. In a related aspect, the invention features compositions which comprise a combination of an anti-Tie2 antibody and a second therapeutic agent. Exemplary agents that may be advantageously combined with an anti-Tie2 antibody include, without limitation, other agents that inhibit anti-Tie2 activity (including other antibodies or antigen-binding fragments thereof, peptide inhibitors, small molecule antagonists, etc.) and/or agents which interfere with Tie2 upstream or downstream signaling.

In yet another aspect, the invention provides methods for inhibiting Tie2 activity using an anti-Tie2 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of Tie2 activity. The anti-Tie2 antibody or antibody fragment of the invention may function to block the interaction between Tie2 and a Tie2 binding partner (e.g., Ang1, Ang2, Ang3, and/or Ang4), or otherwise inhibit the signaling activity of Tie2.

The present invention also includes the use of an anti-Tie2 antibody or antigen binding portion of an antibody of the invention in the manufacture of a medicament for the treatment of a disease or disorder related to or caused by Tie2 activity in a patient.

Other embodiments will become apparent from a review of the ensuing detailed description.

DETAILED DESCRIPTION

Figure 1:
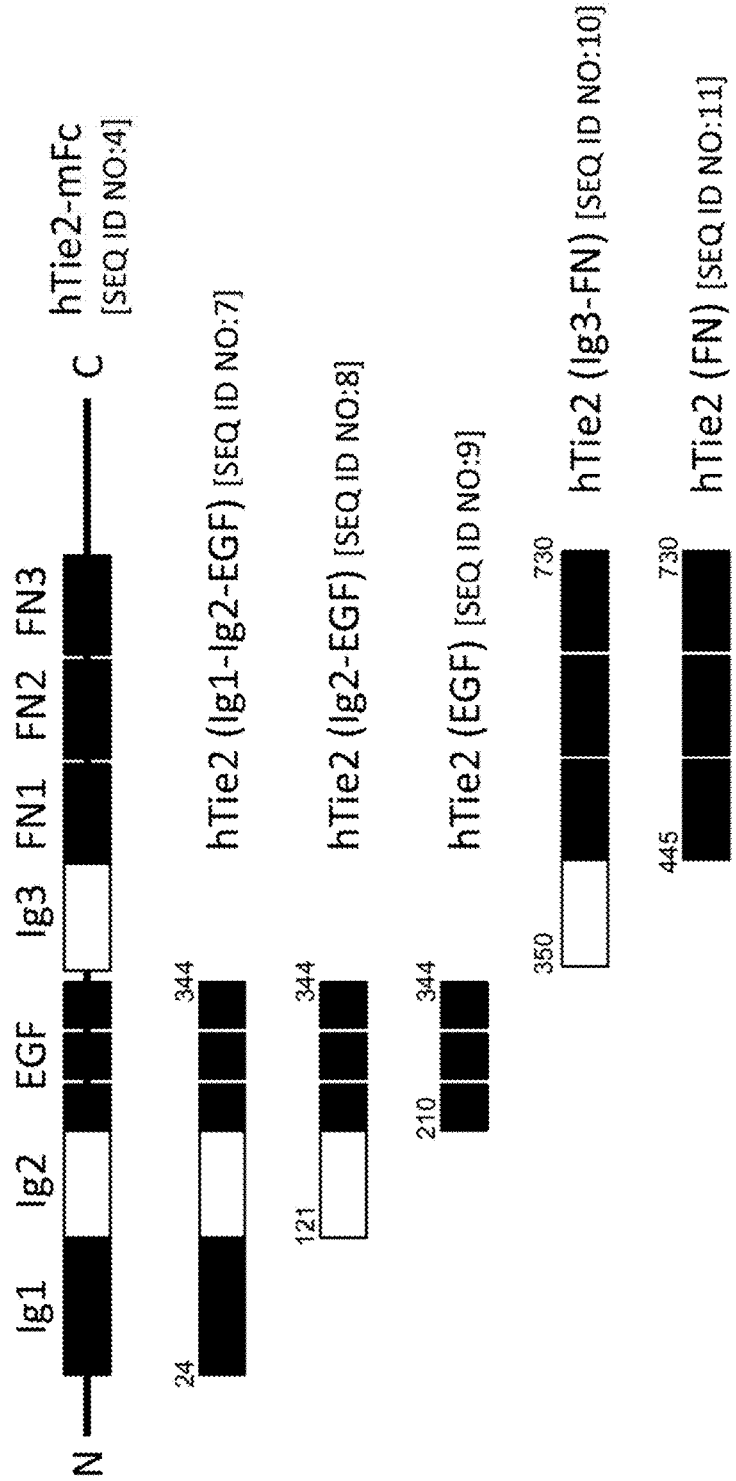
FIG. 1. Linear depiction of full-length human Tie2 and various deletion constructs used to map the epitope of the anti-Tie2 antibodies of the present invention. Numbers above the constructs indicate the amino acid boundaries of the constructs relative to the full-length Tie2 molecule (SEQ ID NO:1).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "Tie2" and "Tie2 fragment," as used herein refer to the human Tie2 protein or fragment unless specified as being from a non-human species (e.g., "mouse Tie2," "mouse Tie2 fragment," "monkey Tie2," "monkey Tie2 fragment," etc.). A "Tie2 fragment" is any portion of Tie2 having fewer amino acids than the full-length Tie2 molecule and which is capable of binding to a Tie2 ligand. Human Tie2 has the amino acid sequence set forth in SEQ ID NO:1. Amino acid sequences of Tie2 molecules from non-human species (e.g., mouse, monkey, rabbit, dog, pig, etc.) are available from public sources such as GenBank (e.g., GenBank accession numbers NP_038718.2 (mouse); NP_001099207.1 (rat); etc).

The term "Tie2 ligand," as used herein, means a protein with which the Tie2 protein interacts to transmit a biological signal in vivo. The term "Tie2 ligand" includes any of the angiopoietins, including, e.g., Ang1, Ang2, Ang3 and/or Ang4. The term "Ang1," as used herein, means a protein comprising the amino acid sequence of SEQ ID NO:15, or a portion thereof which is capable of interacting with Tie2. The term "Ang2," as used herein, means a protein comprising the amino acid sequence of SEQ ID NO:16, or a portion thereof which is capable of interacting with Tie2. The term "Ang3," as used herein, means a protein comprising the amino acid sequence of SEQ ID NO:17, or a portion thereof which is capable of interacting with Tie2. The term "Ang4," as used herein, means a protein comprising the amino acid sequence as set forth in of SEQ ID NO:18, or a portion thereof which is capable of interacting with Tie2.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-Tie2 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" human Tie2, as used in the context of the present invention, includes antibodies that bind human Tie2 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. (See, e.g., Example 2, herein). An isolated antibody that specifically binds human Tie2 may, however, have cross-reactivity to other antigens, such as Tie2 molecules from other (non-human) species.

A "neutralizing" or "blocking" antibody, as used herein, is intended to refer to an antibody whose binding to Tie2: (i) interferes with the interaction between Tie2 or a Tie2 fragment and a Tie2 ligand (e.g., an angiopoietin), and/or (ii) results in inhibition of at least one biological function of Tie2. The inhibition caused by a Tie2 neutralizing or blocking antibody need not be complete so long as it is detectable using an appropriate assay. Exemplary assays for detecting TIE2 inhibition are described herein.

The anti-Tie2 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-Tie2 antibodies comprising variants having one or more conservative substitutions as compared with the HCVR, LCVR and/or CDR amino acid sequences found within the exemplary anti-Tie2 antibodies disclosed herein. For example, the present invention includes anti-Tie2 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences of the anti-Tie2 antibodies disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Biological Characteristics of the Antibodies

The present invention includes antibodies that block the interaction between Tie2 and a Tie2 ligand. As used herein, the expression "blocks the interaction between Tie2 and a Tie2 ligand" means that, in an assay in which the physical interaction between Tie2 and a Tie2 ligand can be detected and/or quantified, the addition of an antibody of the invention reduces the interaction between Tie2 and the Tie2 ligand (e.g., Ang1, Ang2, Ang3 and/or Ang4) by at least 50%. A non-limiting, exemplary assay that can be used to determine if an antibody blocks the interaction between human Tie2 and a Tie2 ligand is illustrated in Example 5, herein. In one exemplary embodiment of this assay format, antibodies are mixed with Tie2 protein, and then the antibody/Tie2 mixture is applied to a surface coated with a Tie 2 ligand (in this case, Ang2 protein). After washing away unbound molecules, the amount of Tie2 bound to the Ang2-coated surface is measured. By using varying amounts of antibody in this assay format, the amount of antibody required to block 50% of Tie2 binding to Ang2 can be calculated and expressed as an $IC_{50}$ value. The format of this assay can be reversed such that Tie2 is coated to surface, antibody is added to the Tie2-coated surface, unbound antibody is washed away, and then a Tie2 ligand is added to the antibody-treated Tie2 surface. The present invention includes anti-Tie2 antibodies that exhibit an $IC_{50}$ of less than about 100 nM when tested in a Tie2/Tie2 ligand binding assay as illustrated in Example 5, or a substantially similar assay. For example, the invention includes anti-Tie2 antibodies that exhibit an $IC_{50}$ of less than about 100, 90, 80, 70, 60, 50, 40, 30, 20, 19, 18, 17, 16, 15, 14, 12, 10, 9, 8, 7, 6, 5, 4, 3, 2, 1, 0.5, 0.4, 0.3, or 0.2 nM when tested in a Tie2/Tie2 ligand binding assay as illustrated in Example 5, or a substantially similar assay.

Another assay format that can be used to determine whether an antibody blocks the interaction between human Tie2 and a Tie2 ligand is illustrated in Example 6, herein. In this assay format, a cell line is used which is engineered to express human Tie2 on its surface, and which also includes a reporter construct that causes a detectable signal to be expressed when Tie2 interacts with a Tie2 ligand. The engineered cells are treated with anti-Tie2 antibodies and with Tie2 ligand and the reporter signal is measured. By using varying amounts of antibody in this assay format, the amount of antibody required to inhibit 50% of the reporter signal observed in the absence of antibody can be calculated and expressed as an $IC_{50}$ value. The present invention includes anti-Tie2 antibodies that exhibit an $IC_{50}$ of less than about 20 nM when tested in a Tie2/Tie2 ligand binding assay as illustrated in Example 6, or a substantially similar assay. For example, the invention includes anti-Tie2 antibodies that exhibit an $IC_{50}$ of less than about 20, 19, 18, 17, 16, 15, 14, 13, 12, 11, 10, 9, 8, 7, 6, 5, 4, 3, 2, 1, 0.5, 0.4, 0.3, 0.2 or 0.1 nM when tested in a Tie2/Tie2 ligand binding assay as described in Example 6, or a substantially similar assay.

Epitope Mapping and Related Technologies

The human Tie2 protein contains the following domains: an Ig1 domain, an Ig2 domain, an EGF repeat domain, an Ig3 domain, and a fibronectin repeat (FN) domain (including FN1, FN2 and FN3). These domains are graphically depicted in FIG. 1. The present invention includes anti-Tie2 antibodies which bind specifically to an epitope within one or more of the following regions: (a) the Ig1-Ig2-EGF domains (SEQ ID NO:7); (b) the Ig2-EGF domains (SEQ ID NO:8); (c) the EGF domain (SEQ ID NO:9); (d) the Ig3-FN domains (SEQ ID NO:10); and/or (e) the FN domains (SEQ ID NO:11). (See Examples 3 and 4).

According to certain embodiments, the present invention provides anti-Tie2 antibodies which interact with one or more amino acids found within the Ig1 and/or Ig2 domains of Tie2. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the Ig1 and/or Ig2 domains of Tie2. Alternatively, the epitope may consist of a plurality of non-contiguous amino acids (or amino acid sequences) located within the Ig1 and/or Ig2 domains of Tie2. According to certain embodiments of the present invention, anti-Tie2 antibodies are provided which interact with one or more amino acids located within one or more amino acid segments selected from the group consisting of amino acids 96-106 of SEQ ID NO:7, amino acids 139-152 of SEQ ID NO:7; and amino acids 166-175 of SEQ ID NO:7. For example, the present invention includes anti-Tie2 antibodies which interact with at least one amino acid within each of the aforementioned segments (i.e., within each of amino acids 96-106, 139-152, and 166-175 of SEQ ID NO:7). According to certain embodiments of the present invention, antibodies which interact with amino acids 139-152 and/or 166-175 of SEQ ID NO:7 are capable of blocking the interaction between Tie2 and one or more Tie2 ligands, such as, e.g., Ang2 (see Examples 4-6, herein).

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. (See, e.g., Example 4 herein). In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention includes anti-Tie2 antibodies that bind to the same epitope as any of the specific exemplary antibodies described herein (e.g., antibodies H1M2055N, and H2aM2760N, produced from deposited cell lines PTA-12295 and PTA-12296, respectively). Likewise, the present invention also includes anti-Tie2 antibodies that compete for binding to Tie2 or a Tie2 fragment with any of the specific exemplary antibodies described herein (e.g., antibodies H1M2055N, and H2aM2760N, produced from deposited cell lines PTA-12295 and PTA-12296, respectively).

One can easily determine whether an antibody binds to the same epitope as, or competes for binding with, a reference anti-Tie2 antibody by using routine methods known in the art. For example, to determine if a test antibody binds to the same epitope as a reference anti-Tie2 antibody of the invention, the reference antibody is allowed to bind to a Tie2 protein or peptide under saturating conditions. Next, the ability of a test antibody to bind to the Tie2 molecule is assessed. If the test antibody is able to bind to Tie2 following saturation binding with the reference anti-Tie2 antibody, it can be concluded that the test antibody binds to a different epitope than the reference anti-Tie2 antibody. On the other hand, if the test antibody is not able to bind to the Tie2 molecule following saturation binding with the reference anti-Tie2 antibody, then the test antibody may bind to the same epitope as the epitope bound by the reference anti-Tie2 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-Tie2 antibody, the above-described binding methodology is performed in two orientations: In a first orientation, the reference antibody is allowed to bind to a Tie2 molecule under saturating conditions followed by assessment of binding of the test antibody to the Tie2 molecule. In a second orientation, the test antibody is allowed to bind to a Tie2 molecule under saturating conditions followed by assessment of binding of the reference antibody to the Tie2 molecule. If, in both orientations, only the first (saturating) antibody is capable of binding to the Tie2 molecule, then it is concluded that the test antibody and the reference antibody compete for binding to Tie2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human Tie2.

Using VELOCIMMUNE™ technology or any other known method for generating monoclonal antibodies, high affinity chimeric antibodies to Tie2 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-Tie2 antibodies and antibody fragments of the present invention encompass proteins having amino acid sequences that vary from those of the described antibodies but that retain the ability to bind human Tie2. Such variant antibodies and antibody fragments comprise one or more additions, deletions, or substitutions of amino acids when compared to parent sequence, but exhibit biological activity that is essentially equivalent to that of the described antibodies. Likewise, the anti-Tie2 antibody-encoding DNA sequences of the present invention encompass sequences that comprise one or more additions, deletions, or substitutions of nucleotides when compared to the disclosed sequence, but that encode an anti-Tie2 antibody or antibody fragment that is essentially bioequivalent to an anti-Tie2 antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-Tie2 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-Tie2 antibody variants comprising amino acid changes which modify the glycosylation characteristics of the antibodies, e.g., mutations which eliminate or remove glycosylation.

Species Selectivity and Species Cross-Reactivity

According to certain embodiments of the invention, the anti-Tie2 antibodies bind to human Tie2 but not to Tie2 from other species. The present invention also includes anti-Tie2 antibodies that bind to human Tie2 and to Tie2 from one or more non-human species. For example, the anti-Tie2 antibodies of the invention may specifically bind to human Tie2 as well as to a rodent Tie2 (e.g., Tie2 from mouse or rat). An exemplary construct that can be used to determine whether an antibody specifically binds mouse Tie2 is the construct having the amino acid sequence of SEQ ID NO:6; an exemplary construct that can be used to determine whether an antibody specifically binds rat Tie2 is the construct having the amino acid sequence of SEQ ID NO:5. The use of these constructs to assess anti-Tie2 antibody binding is illustrated in Example 2, herein.

Immunoconjugates

The invention encompasses anti-Tie2 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-Tie2 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human Tie2 or a fragment thereof, and the other arm of the immunoglobulin is specific for a second therapeutic target or is conjugated to a therapeutic moiety such as a trypsin inhibitor.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides pharmaceutical compositions comprising the anti-Tie2 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with Tie2 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering Tie2 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with Tie2 activity, including diseases or disorders associated with angiogenesis. The antibodies and antigen-binding fragments of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the invention are used to treat one or more of the following cancers: renal cell carcinoma, pancreatic carcinoma, breast cancer, prostate cancer, malignant gliomas, osteosarcoma, colorectal cancer, malignant mesothelioma, multiple myeloma, ovarian cancer, small cell lung cancer, non-small cell lung cancer, synovial sarcoma, thyroid cancer, or melanoma.

Combination Therapies

The present invention includes therapeutic administration regimens which comprise administering an anti-Tie2 antibody of the present invention in combination with at least one additional therapeutically active component. Non-limiting examples of such additional therapeutically active components include, for example, another Tie2 antagonist (e.g., an anti-Tie2 antibody), an antagonist of epidermal growth factor receptor (EGFR) (e.g., anti-EGFR antibody [e.g., cetuximab or panitumumab] or small molecule inhibitor of EGFR activity [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), etc. Other agents that may be beneficially administered in combination with the anti-Tie2 antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention also includes therapeutic combinations comprising any of the anti-Tie2 antibodies mentioned herein and an inhibitor of one or more of VEGF, Ang2, DLL4, ErbB2, ErbB3, ErbB4, EGFRvIII, cMet, IGF1R, B-raf, PDGFR-α, PDGFR-β, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The anti-Tie2 antibodies of the invention may also be administered in combination with antivirals, antibiotics, analgesics, corticosteroids and/or NSAIDs. The anti-Tie2 antibodies of the invention may also be administered as part of a treatment regimen that also includes radiation treatment and/or conventional chemotherapy.

The additional therapeutically active component(s) may be administered just prior to, concurrent with, or shortly after the administration of an anti-Tie2 antibody of the present invention; (for purposes of the present disclosure, such administration regimens are considered the administration of an anti-Tie2 antibody "in combination with" an additional therapeutically active component). The present invention includes pharmaceutical compositions in which an anti-Tie2 antibody of the present invention is co-formulated with one or more of the additional therapeutically active component(s) as described elsewhere herein.

Diagnostic Uses of the Antibodies

The anti-Tie2 antibodies of the present invention may also be used to detect and/or measure Tie2 in a sample, e.g., for diagnostic purposes. For example, an anti-Tie2 antibody, or fragment thereof, may be used to diagnose a condition or disease characterized by aberrant expression (e.g., over-expression, under-expression, lack of expression, etc.) of Tie2. Exemplary diagnostic assays for Tie2 may comprise, e.g., contacting a sample, obtained from a patient, with an anti-Tie2 antibody of the invention, wherein the anti-Tie2 antibody is labeled with a detectable label or reporter molecule. Alternatively, an unlabeled anti-Tie2 antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure Tie2 in a sample include enzyme-linked immunosorbent assay (ELISA), radioimmunoassay (RIA), and fluorescence-activated cell sorting (FACS).

Samples that can be used in Tie2 diagnostic assays according to the present invention include any tissue or fluid sample obtainable from a patient which contains detectable quantities of Tie2 protein, or fragments thereof, under normal or pathological conditions. Generally, levels of Tie2 in a particular sample obtained from a healthy patient (e.g., a patient not afflicted with a disease or condition associated with abnormal Tie2 levels or activity) will be measured to initially establish a baseline, or standard, level of Tie2. This baseline level of Tie2 can then be compared against the levels of Tie2 measured in samples obtained from individuals suspected of having a Tie2 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Control Constructs Used in the Following Examples

An exemplary control construct (anti-Tie2 antibody) was included in several experiments described below for comparative purposes. The antibody, referred to as Control I, is a chimeric anti-Tie2 antibody with mouse heavy and light chain variable domains having the amino acid sequences of the corresponding domains of "12H8", as set forth in U.S. Pat. No. 6,376,653. The constant domain of this antibody is human IgG4.

Example 1

Generation of Human Antibodies to Human Tie2

Several human anti-Tie2 antibodies were generated by immunizing a VELOCIMMUNE® mouse with human Tie2 antigen according to standard methods (see, e.g., U.S. Pat. No. 6,596,541). Using this technique, several anti-Tie2 antibodies were obtained; exemplary antibodies generated in this manner, and their corresponding biological characteristics, are described in detail in the following Examples and include the antibodies designated H2aM2760N, H2aM2761N, H1M2055N, H1H2304B, H1H2317B, H1H2322B, H1H2324B, H1H2331B, H1H2332B, H1H2333S, H1H2337B, H1H2338B, H1H2339B, H1H2340B, and H4H2055N. The H1M, H2M, H1H, etc. prefixes on the antibody designations used herein indicate the particular Fc region of the antibody. For example, an "H2M" antibody has a mouse IgG2 Fc, whereas an "H1H" antibody has a human IgG1 Fc. As will be appreciated by a person of ordinary skill in the art, an Fc region of an antibody can be modified or replaced with a different Fc region, but the variable domains (including the CDRs) will remain the same.

Hybridomas which produce the anti-Tie2 antibodies H1M2055N, and H2aM2760N were deposited under terms in accordance with the Budapest Treaty with the American Type Culture Collection (ATCC), 10801 University Blvd., Manassas, Va. 20110-2209 on Dec. 2, 2011, under accession numbers PTA-12295 (H1M2055N) and PTA-12296 (H2aM2760N).

Example 2

Surface Plasmon Resonance Derived Binding Affinities and Kinetic Constants of Human Monoclonal Anti-Tie2 Antibodies Binding affinities and kinetic constants of human monoclonal anti-Tie2 antibodies were determined by surface plasmon resonance at 25° C. and 37° C. (Tables 1-4). Measurements were conducted on a Biacore 2000 or T200 instrument.

For antibodies with a mouse constant region (designated H1M or H2M), antibodies were immobilized onto an anti-mouse Fc sensor surface and different concentrations of human, mouse or rat Tie2 constructs (hTie2-His, mTie2-hFc and rTie2-hFc) were injected over the antibody captured surface. For antibodies in the human IgG format (designated H1H or H4H), either an anti-human Fc sensor surface (hTie2-His and hTie2-mFc) or anti-human Fab sensor surface (mTie2-hFc and rTie2-hFc) was employed depending on the Tie-2 construct applied to the antibody captured surface. Amino acid sequences of the constructs used in this Example are as follows: hTie2-His (SEQ ID NO:2); hTie2-hFc (SEQ ID NO:3); hTie2-mFc (SEQ ID NO:4); rTie2-hFc (SEQ ID NO:5); and mTie2-hFc (SEQ ID NO:6).

Kinetic rate constants—association rate (ka) and dissociation rate (kd) were determined by fitting the real time binding sensorgrams to a 1:1 binding model with mass transport limitation using Scrubber 2.0 curve fitting software. The equilibrium dissociation constant ($K_D$) and dissociative half-life (T½) were calculated from the kinetic rate constants as: $K_D$ (M)=kd/ka; and T½ (min)=(In2/(60*kd).). As shown in Tables 1-2, several antibodies demonstrated high affinity binding to hTie2 at both temperatures tested. In addition H1M2055N, H1H2332B, H1H2337B, H1H2340B and H4H2055N exhibited significant binding to mouse and rat Tie2 (Tables 3-4).

TABLE 1

Biacore binding affinities of human mAbs to hTie2 at 25° C.
Binding at 25° Mab capture format

| Antibody | Analyte | ka (Ms$^{-1}$) | kd (s$^{-1}$) | K$_D$ (Molar) | T½ (min) |
|---|---|---|---|---|---|
| H2aM2760N | hTie2-His | 2.91E+04 | 1.84E-04 | 6.32E-09 | 63 |
|  | hTie2-hFc | NT | NT | NT | NT |
| H2aM2761N | hTie2-His | 3.33E+04 | 1.01E-04 | 3.02E-09 | 115 |
|  | hTie2-hFc | NT | NT | NT | NT |
| H1M2055N | hTie2-His | 5.75E+05 | 1.34E-04 | 2.33E-10 | 86 |
|  | hTie2-hFc | NT | NT | NT | NT |
| H1H2304B | hTie2-His | 1.99E+05 | 1.32E-03 | 6.66E-09 | 9 |
|  | hTie2-mFc | 5.80E+05 | 3.75E-05 | 6.46E-11 | 308 |
| H1H2317B | hTie2-His | 1.43E+05 | 9.26E-04 | 6.50E-09 | 12 |
|  | hTie2-mFc | 3.90E+05 | 2.36E-05 | 6.10E-11 | 489 |
| H1H2322B | hTie2-His | 1.67E+05 | 9.76E-04 | 5.84E-09 | 12 |
|  | hTie2-mFc | 4.80E+05 | 1.39E-05 | 2.90E-11 | 829 |
| H1H2324B | hTie2-His | 2.40E+05 | 9.25E-04 | 3.86E-09 | 12 |
|  | hTie2-mFc | 6.30E+05 | 5.92E-05 | 9.39E-11 | 195 |
| H1H2331B | hTie2-His | 3.63E+04 | 1.17E-03 | 3.22E-08 | 10 |
|  | hTie2-mFc | 8.20E+04 | 1.24E-04 | 1.52E-09 | 93 |
| H1H2332B | hTie2-His | 8.89E+04 | 2.23E-03 | 2.51E-08 | 5 |
|  | hTie2-mFc | 1.25E+05 | 2.13E-04 | 1.1E-09 | 54 |
| H1H2333S | hTie2-His | 5.92E+04 | 3.09E-04 | 5.21E-09 | 37 |
|  | hTie2-mFc | NB | NB | NB | NB |
| H1H2337B | hTie2-His | 6.47E+04 | 6.49E-04 | 1.00E-08 | 18 |
|  | hTie2-mFc | 1.20E+05 | 1.11E-04 | 9.30E-10 | 104 |
| H1H2338B | hTie2-His | 4.93E+04 | 3.44E-04 | 6.99E-09 | 34 |
|  | hTie2-mFc | NB | NB | NB | NB |
| H1H2339B | hTie2-His | 5.58E+04 | 1.25E-03 | 2.24E-08 | 9 |
|  | hTie2-mFc | 1.51E+05 | 1.02E-04 | 6.70E-10 | 114 |
| H1H2340B | hTie2-His | 7.01E+04 | 3.45E-03 | 4.92E-08 | 3 |
|  | hTie2-mFc | 1.65E+05 | 1.91E-04 | 1.16E-09 | 60 |
| H4H2055N | hTie2-His | 3.82E+05 | 4.84E-04 | 1.27E-09 | 24 |
|  | hTie2-mFc | 1.27E+06 | 9.92E-05 | 7.80E-11 | 116 |
| Control I | hTie2-His | 6.53E+04 | 4.57E-04 | 7.00E-09 | 25 |
|  | hTie2-mFc | 1.45E+05 | 1.16E-04 | 8.03E-10 | 99 |

NB = no binding under the conditions tested
NT = not tested

TABLE 2

Biacore binding affinities of human mAbs to hTie2 at 37° C.
Binding at 37° Mab capture format

| Antibody | Analyte | ka (Ms$^{-1}$) | kd (s$^{-1}$) | K$_D$ (Molar) | T½ (min) |
|---|---|---|---|---|---|
| H2aM2760N | hTie2-His | 4.04E+04 | 3.06E-04 | 7.60E-09 | 38 |
|  | hTie2-hFc | NT | NT | NT | NT |
| H2aM2761N | hTie2-His | 4.26E+04 | 2.87E-04 | 6.74E-09 | 40 |
|  | hTie2-hFc | NT | NT | NT | NT |
| H1M2055N | hTie2-His | 1.08E+06 | 3.36E-04 | 3.10E-10 | 34 |
|  | hTie2-hFc | NT | NT | NT | NT |
| H1H2304B | hTie2-His | 3.50E+05 | 3.67E-03 | 1.05E-08 | 3 |
|  | hTie2-mFc | 6.60E+05 | 1.30E-04 | 1.96E-10 | 89 |
| H1H2317B | hTie2-His | 1.74E+05 | 3.46E-03 | 1.98E-08 | 3 |
|  | hTie2-mFc | 4.60E+05 | 9.94E-05 | 2.15E-10 | 116 |
| H1H2322B | hTie2-His | 2.12E+05 | 4.74E-03 | 2.23E-08 | 2 |
|  | hTie2-mFc | 5.70E+05 | 9.72E-05 | 1.72E-10 | 119 |
| H1H2324B | hTie2-His | 2.78E+05 | 2.26E-04 | 8.12E-09 | 5 |
|  | hTie2-mFc | 7.40E+05 | 1.47E-04 | 1.99E-10 | 79 |
| H1H2331B | hTie2-His | 5.48E+04 | 4.74E-03 | 8.65E-08 | 2 |
|  | hTie2-mFc | 1.28E+05 | 1.99E-04 | 1.56E-09 | 58 |
| H1H2332B | hTie2-His | 9.58E+04 | 8.19E-03 | 8.55E-08 | 1 |
|  | hTie2-mFc | 1.81E+05 | 6.52E-04 | 3.60E-09 | 18 |
| H1H2333S | hTie2-His | 6.20E+04 | 9.83E-04 | 1.58E-08 | 12 |
|  | hTie2-mFc | NB | NB | NB | NB |
| H1H2337B | hTie2-His | 8.35E+04 | 2.41E-03 | 2.89E-08 | 5 |
|  | hTie2-mFc | 1.92E+05 | 2.55E-04 | 1.33E-09 | 45 |
| H1H2338B | hTie2-His | 5.55E+04 | 9.93E-04 | 1.79E-08 | 12 |
|  | hTie2-mFc | NB | NB | NB | NB |

TABLE 2-continued

Biacore binding affinities of human mAbs to hTie2 at 37° C.
Binding at 37° Mab capture format

| Antibody | Analyte | ka (Ms$^{-1}$) | kd (s$^{-1}$) | K$_D$ (Molar) | T½ (min) |
|---|---|---|---|---|---|
| H1H2339B | hTie2-His | 6.78E+04 | 4.88E-03 | 7.20E-08 | 2 |
|  | hTie2-mFc | 1.93E+05 | 2.95E-04 | 1.53E-09 | 39 |
| H1H2340B | hTie2-His | 9.75E+04 | 9.98E-03 | 1.02E-07 | 1 |
|  | hTie2-mFc | 2.00E+05 | 5.15E-04 | 2.58E-09 | 22 |
| H4H2055N | hTie2-His | 5.49E+05 | 8.01E-04 | 1.46E-09 | 14 |
|  | hTie2-mFc | 1.67E+06 | 1.55E-04 | 9.30E-11 | 74 |
| Control I | hTie2-His | 7.48E-04 | 1.12E-03 | 1.49E-08 | 10 |
|  | hTie2-mFc | 1.80E+05 | 1.70E-04 | 9.40E-10 | 68 |

NB = no binding under the conditions tested
NT = not tested

TABLE 3

Biacore binding affinities of human mAbs to mTie2 at 25° C.
Binding at 25° Mab capture format

| Antibody | Analyte | ka (Ms$^{-1}$) | kd (s$^{-1}$) | K$_D$ (Molar) | T½ (min) |
|---|---|---|---|---|---|
| H2aM2760N | mTie2-hFc | NB | NB | NB | NB |
| H2aM2761N | mTie2-hFc | NB | NB | NB | NB |
| H1M2055N | mTie2-hFc | 1.07E+06 | 1.85E-05 | 1.73E-11 | 625 |
| H1H2304B | mTie2-hFc | NB | NB | NB | NB |
| H1H2317B | mTie2-hFc | NB | NB | NB | NB |
| H1H2322B | mTie2-hFc | NB | NB | NB | NB |
| H1H2324B | mTie2-hFc | NB | NB | NB | NB |
| H1H2331B | mTie2-hFc | 4.81E+04 | 2.72E-03 | 5.65E-08 | 4 |
| H1H2332B | mTie2-hFc | 5.39E+04 | 5.76E-03 | 1.07E-07 | 2 |
| H1H2333S | mTie2-hFc | NB | NB | NB | NB |
| H1H2337B | mTie2-hFc | 1.87E+05 | 1.84E-02 | 9.83E-08 | 1 |
| H1H2338B | mTie2-hFc | NB | NB | NB | NB |
| H1H2339B | mTie2-hFc | 4.68E+04 | 2.63E-03 | 5.63E-08 | 4 |
| H1H2340B | mTie2-hFc | 1.36E_05 | 6.72E-03 | 4.96E-08 | 2 |
| H4H2055N | mTie2-hFc | 1.24E+06 | 6.19E-06 | 5.01E-12 | 1867 |
| Control I | mTie2-hFc | NB | NB | NB | NB |

NB = no binding under the conditions tested

TABLE 4

Biacore binding affinities of human mAbs to rTie2 at 25° C.
Binding at 25° C. Mab capture format

| Antibody | Analyte | ka (Ms$^{-1}$) | kd (s$^{-1}$) | K$_D$ (Molar) | T½ |
|---|---|---|---|---|---|
| H2aM2760N | rTie2-hFc | NB | NB | NB | NB |
| H2aM2761N | rTie2-hFc | NB | NB | NB | NB |
| H1M2055N | rTie2-hFc | 9.43E+05 | 2.55E-05 | 2.70E-11 | 454 |
| H1H2304B | rTie2-hFc | NB | NB | NB | NB |
| H1H2317B | rTie2-hFc | NB | NB | NB | NB |
| H1H2322B | rTie2-hFc | NB | NB | NB | NB |
| H1H2324B | rTie2-hFc | NB | NB | NB | NB |
| H1H2331B | rTie2-hFc | NB | NB | NB | NB |
| H1H2332B | rTie2-hFc | 1.12E+05 | 6.18E-03 | 5.53E-08 | 2 |
| H1H2333S | rTie2-hFc | NB | NB | NB | NB |
| H1H2337B | rTie2-hFc | 1.45E+05 | 8.46E-03 | 5.85E-08 | 1 |
| H1H2338B | rTie2-hFc | NB | NB | NB | NB |
| H1H2339B | rTie2-hFc | NB | NB | NB | NB |
| H1H2340B | rTie2-hFc | 1.43E+05 | 3.71E-03 | 2.59E-08 | 3 |
| H4H2055N | rTie2-hFc | 1.07E+06 | 1.00E-06 | 9.31E-13 | 11550 |
| Control I | rTie2-hFc | NB | NB | NB | NB |

NB = no binding under the conditions tested

Example 3

Epitope Mapping of Tie2 mAbs using Luminex Beads

To determine domain binding for the anti-Tie2 antibodies, several hTie2 receptor extracellular domain-deletion constructs were covalently linked to luminex xMAP beads (10 µg/ml of each protein per $10^7$ beads). The constructs are depicted in FIG. 1 and are designated as follows: hTie2 (Ig1-Ig2-EGF) (SEQ ID NO:7); hTie2 (Ig2-EGF) (SEQ ID NO:8); hTie2 (EGF) (SEQ ID NO:9); hTie2 (Ig3-FN) (SEQ ID NO:10); and hTie2 (FN) (SEQ ID NO:11). Also tested in this Example were full-length hTie2-mFc (SEQ ID NO:4) and hTie1-hFc (SEQ ID NO:12) ectodomain constructs.

For binding, 25 µl of anti-Tie2 antibody (25 µg/ml) was added to 75 µl of the above created Luminex bead mixture ($3 \times 10^3$ beads per construct) in binding buffer (PBS, 0.05% Tween 20, 1 mg/ml BSA, 0.05% sodium azide) into a 96 well filter plate (Millipore). Incubation was at room temperature (RT) for 90 min or overnight at 4° C. with shaking. The beads were washed 3× with washing buffer (PBS+ 0.05% Tween 20) resuspended in 100 µl binding buffer containing PE (phycoerythrine)-labeled anti human kappa or PE-labeled anti mouse Fab secondary antibody and incubated at RT for 45 min with shaking. Samples were washed 2× more and binding signal (MFI) for each bead was determined using a Luminex L200 or FLEXMAP3D instrument. Bead linked human Tie2 was used as positive control and bead linked human Tie1 was used to measure family cross-reactivity. In general MFI signals greater than 500 units represent significant binding. Results are summarized in Table 5.

Example 4

Epitope Mapping of H4H2055N Binding to Tie2 by H/D Exchange

Experiments were conducted to more precisely define the amino acid residues of Tie2 with which H4H2055N interacts. (H4H2055N is a fully human IgG4 version of the antibody H1M2055N produced from hybridoma PTA-12295.) For this purpose H/D exchange epitope mapping was carried out. A general description of the H/D exchange method is set forth in e.g., Ehring (1999) *Analytical Biochemistry* 267(2):252-259; and Engen and Smith (2001) *Anal. Chem.* 73:256A-265A.

To map the binding epitope(s) of antibody H4H2055N on Tie2 via H/D exchange, a recombinant construct consisting of the Ig1, Ig2 and EGF extracellular domains of human Tie2 (hTie2 (Ig1-Ig2-EGF); SEQ ID NO:7) was used. Antibody H4H2055N was covalently attached to N-hydroxysuccinimide (NHS) agarose beads (GE Lifescience).

In the 'on-solution/off-beads' experiment (on-exchange in solution followed by off-exchange on beads), the ligand (hTie2 Ig1-Ig2-EGF) was deuterated for 5 min or 10 min in PBS buffer prepared with $D_2O$, and then bound to H4H2055N beads through a 2 min incubation. The Tie2-bound beads were washed with PBS aqueous buffer (prepared with $H_2O$) and incubated for half of the on-exchange time in PBS buffer. After the off-exchange, the bound Tie2 was eluted from beads with an ice-cold low pH TFA solution. The eluted Tie2 was then digested with immobilized pepsin (Thermo Scientific) for 5 min. The resulting peptides were desalted using ZipTip® chromatographic pipette tips and immediately analyzed by UltrafleXtreme matrix assisted laser desorption ionization time of flight (MALDI-TOF) mass spectrometry (MS).

In the 'on-beads/off-beads' experiment (on-exchange on beads followed by off-exchange on beads), Tie2 was first bound to H4H2055N beads and then incubated for 5 min or

TABLE 5

| Antibody | hTie2-mFc | hTie1-hFc | hTie2 (EGF) | hTie2 (Ig1, Ig2, EGF) | hTie2 (Ig2, EGF) | hTie2 (FN)-hFc | hTie2 (Ig3, FN)-hFc | Predicted Binding Domain |
|---|---|---|---|---|---|---|---|---|
| H2aM2760N | 1668 | 15 | 4 | 9392 | 6245 | 341 | 330 | Ig1, Ig2 |
| H2aM2761N | 8503 | 135 | 10205 | 11657 | 8568 | 3403 | 14509 | EGF, Ig3 |
| H1M2055N | 753 | 112 | 90 | 2022 | 873 | 43 | 40 | Ig1, Ig2 |
| H1H2304B | 4250 | 40 | 8901 | 8776 | 7648 | 5 | 6 | EGF repeat |
| H1H2317B | 4853 | 37 | 9611 | 8966 | 8325 | 9 | 11 | EGF repeat |
| H1H2322B | 4040 | 47 | 9901 | 9161 | 9167 | 10 | 13 | EGF repeat |
| H1H2324B | 4506 | 31 | 9773 | 9438 | 8686 | 7 | 10 | EGF repeat |
| H1H2331B | 5766 | 118 | 8 | 6 | 10 | 8097 | 6568 | FN repeat |
| H1H2332B | 4783 | 32 | 3 | 3 | 4 | 6711 | 6044 | FN repeat |
| H1H2333S | 1875 | 10 | 3 | 2 | 2 | 6 | 6 | ND |
| H1H2337B | 5208 | 48 | 9 | 7 | 9 | 6425 | 7368 | FN repeat |
| H1H2338B | 1385 | 9 | 4 | 5 | 5 | 6 | 8 | ND |
| H1H2339B | 2913 | 62 | 6 | 5 | 6 | 4529 | 3838 | FN repeat |
| H1H2340B | 3009 | 22 | 4 | 4 | 6 | 5149 | 4599 | FN repeat |
| Control I | 4901 | 7 | 3 | 4 | 5 | 6105 | 4554 | FN repeat |

ND = not determined

From the above results, it can be concluded that H2aM2760N and H1M2055N bind to the Ig1/Ig2 domains of Tie2; H2aM2761N binds to the EGF and Ig3 domains of Tie2; H1H2304B, H1H2317B, H1H2322B and H1H2324B bind to the EGF domain of Tie2; and H1H2331B, H1H2332B, H1H2337B, H1H2339B, H1H2340B, and Control I bind to the FN domain of Tie2.

10 min in $D_2O$ for on-exchange. The following steps (off-exchange, pepsin digestion, and MS analysis) were carried out as described for the 'on-solution/off-beads' procedure. The centroid values or average mass-to-charge ratios (m/z) of all the detected peptides were calculated and compared between these two sets of experiments.

The results are summarized in Table 6 which provides a comparison of the centroid m/z values for all the detected peptides identified by liquid chromatography-matrix assisted laser desorption ionization (LC-MALDI) MS following the H/D exchange and peptic digest procedure. Likely due to disulfide bonds, the Tie2 sequence coverage detected from a single MALDI-TOF spectrum is relatively low. Nevertheless, more than half of the detected peptic peptides gave similar centroid values for both the on-solution/off-beads and on-beads/off-beads protocols. Three segments with corresponding residues 88-106, 139-152, and 166-175 had delta centroid values≥0.20 m/z in both experiments. For purposes of the present Example a positive difference (Δ) of at least 0.20 m/z in both experiments indicates amino acids protected by antibody binding. Segments meeting this criterion are indicated by bold text and an asterisk (*) in Table 6.

TABLE 6

H4H2055N Binding to Tie2

| Residues (of SEQ ID NO: 7) | Experiment I 5 min on-/2.5 min off-exchange | | | Experiment II 10 min on-/5 min off-exchange | | |
|---|---|---|---|---|---|---|
| | On-solution/ Off Beads | On-Beads/ Off-Beads | Δ | On-solution/ Off Beads | On-Beads/ Off-Beads | Δ |
| 20-33 | 1568.70 | 1568.63 | 0.07 | 1568.63 | 1568.63 | 0.00 |
| 26-33 | 1036.17 | 1036.16 | 0.01 | 1036.27 | 1036.21 | 0.07 |
| 38-50 | 1572.91 | 1572.93 | −0.02 | 1572.78 | 1572.98 | −0.20 |
| 39-50 | 1425.38 | 1425.39 | 0.00 | 1425.54 | 1425.45 | 0.08 |
| 42-53 | 1440.52 | 1440.44 | 0.09 | 1440.62 | 1440.52 | 0.10 |
| 42-58 | 2041.43 | 2041.42 | 0.01 | 2041.58 | 2041.41 | 0.17 |
| 78-87 | 1124.17 | 1124.15 | 0.03 | 1124.20 | 1124.14 | 0.07 |
| 88-95 | 1049.48 | 1049.46 | 0.02 | 1049.46 | 1049.54 | −0.08 |
| 88-101* | 1767.78 | 1767.51 | 0.27 | 1767.79 | 1767.57 | 0.22 |
| 88-102* | 1881.08 | 1880.66 | 0.42 | 1881.14 | 1880.69 | 0.45 |
| 93-101* | 1127.80 | 1127.57 | 0.24 | 1127.80 | 1127.61 | 0.19 |
| 93-102* | 1241.46 | 1240.83 | 0.63 | 1241.34 | 1240.83 | 0.51 |
| 96-102* | 850.54 | 850.22 | 0.32 | 850.55 | 850.25 | 0.30 |
| 96-106* | 1233.29 | 1232.66 | 0.64 | 1233.43 | 1232.65 | 0.78 |
| 139-151* | 1514.22 | 1513.16 | 1.06 | 1514.49 | 1513.21 | 1.28 |
| 139-152* | 1643.17 | 1642.02 | 1.16 | 1643.44 | 1642.06 | 1.38 |
| 152-165 | 1498.87 | 1498.73 | 0.14 | 1498.88 | 1498.77 | 0.11 |
| 152-166 | 1662.09 | 1662.01 | 0.07 | 1662.10 | 1662.08 | 0.02 |
| 153-165 | 1369.70 | 1369.64 | 0.06 | 1369.77 | 1369.66 | 0.11 |
| 166-175* | 1115.07 | 1114.59 | 0.47 | 1115.04 | 1114.65 | 0.39 |
| 167-175* | 951.73 | 951.30 | 0.42 | 951.74 | 951.33 | 0.41 |

Since the peptide fragment (m/z of 1049.4) corresponding to residues 88-95 did not show deuteron retention (Δ=0) after off-exchange, the first protected segment (88-106) can be reduced to only include residues 96-106. Thus the three regions 96-106, 139-152, and 166-175 of SEQ ID NO:7 are protected from full off-exchange by H4H2055N binding to Tie2 after on-exchange.

The Ig1 domain of Tie2 consists of amino acids 1-97 of SEQ ID NO:7; the Ig2 domain of Tie 2 consists of amino acids 98-186 of SEQ ID NO:7; and the EGF repeat domain consists of amino acids 187-321 of SEQ ID NO:7. Thus the first binding region (amino acids 96-106 of SEQ ID NO:7) includes the last two amino acids of the Ig1 domain and the first 9 amino acids of the Ig2 domain. The second and third binding regions (amino acids 139-152 and 166-175 of SEQ ID NO:7) are located entirely within the Ig2 domain.

It should also be noted that the second and third binding regions (amino acids 139-152 and 166-175 of SEQ ID NO:7) lie within the amino acid region of Tie 2 that directly contacts its cognate ligand, Angiopoietin-2, based on the co-crystal structure by Barton et al. (2006, Nat Struct Mol Biol 13(6) 524-532). Therefore, this example suggests that antibody H4H2055N binds a discontinuous epitope primarily within the Ig2 domain of human Tie2 (with one or two potential amino acid contacts within the C-terminal portion of the Ig1 domain), and that binding to these regions correlates with the ability of H4H2055N to block the interaction between Tie2 and Ang2 as illustrated in Examples 5 and 6 herein.

Example 5

Assessment of the Ability of Anti-Tie2 Antibodies to Block the Interaction Between Tie2 and Angiopoietins Tie2 is known to interact with angiopoietins (Ang1, Ang2, Ang3 and Ang4). An initial set of experiments was therefore conducted to evaluate the ability of anti-Tie2 antibodies to block Tie2 binding to Ang2. In this first set of experiments, a quantitative blocking immunoassay was utilized. Briefly, solutions of 0.8 nM biotinylated ecto-Tie2 fused to 6xHis (SEQ ID NO:2) were premixed with anti-Tie2 antibody ranging from ~50 nM to 0 nM in serial dilutions. After a 1-hour incubation at room temperature, the amount of Tie2-His bound to plate coated Bow-Ang2 was measured by sandwich ELISA. Bow-Ang2 (SEQ ID NO:13), an Ang2 construct that comprises the Fc domain of hIgG1 flanked by one FD domain of Ang2 at both termini, was coated at 2 μg/ml on a 96 well microtiter plate and blocked with BSA. Plate-bound biotin-Tie2-His was detected using HRP conjugated streptavidin, and developed using BD OptEIA™ (BD Biosciences Pharmingen, San Diego, Calif.). Signals of $OD_{450}$ nm were recorded and data was analyzed using GraphPad Prism to calculate $IC_{50}$ values. Results are summarized in Table 7. $IC_{50}$s were defined as the amount of antibody required to reduce 50% of biotin-Tie2-His detectable to plate bound Bow-Ang2 ligand. In Table 7, an antibody is designated an "enhancer" if the addition of the antibody increases the amount of Tie2-His bound to the Bow-Ang2-coated surface relative to the no antibody control.

TABLE 7

$IC_{50}$ values for anti-Tie2 Mabs blocking of hTie2 to plate bound Bow-Ang2

| Antibody | Result in Blocking ELISA | Blocking of binding to Bow-Ang2 $IC_{50}$ (M) |
|---|---|---|
| H2aM2760N | Enhancer | N/A |
| H2aM2761N | Enhancer | N/A |
| H1M2055N | Enhancer | N/A |
| H1H2304B | Enhancer | N/A |
| H1H2317B | Enhancer | N/A |
| H1H2322B | Enhancer | N/A |
| H1H2324B | Enhancer | N/A |
| H1H2331B | Enhancer | N/A |
| H1H2332B | Enhancer | N/A |
| H1H2333S | Enhancer | N/A |
| H1H2337B | Enhancer | N/A |
| H1H2338B | Enhancer | N/A |
| H1H2339B | Blocker | 1.89E−10 |
| H1H2340B | Blocker | 1.03E−09 |
| H4H2055N | Blocker | 1.06E−09 |
| Control I | Enhancer | N/A |

This first set of experiments demonstrates that anti-Tie2 antibodies H1H2339B, H1H2340B and H4H2055N are able to block the interaction between Ang2 and Tie2 in an ELISA format.

Figure 2:
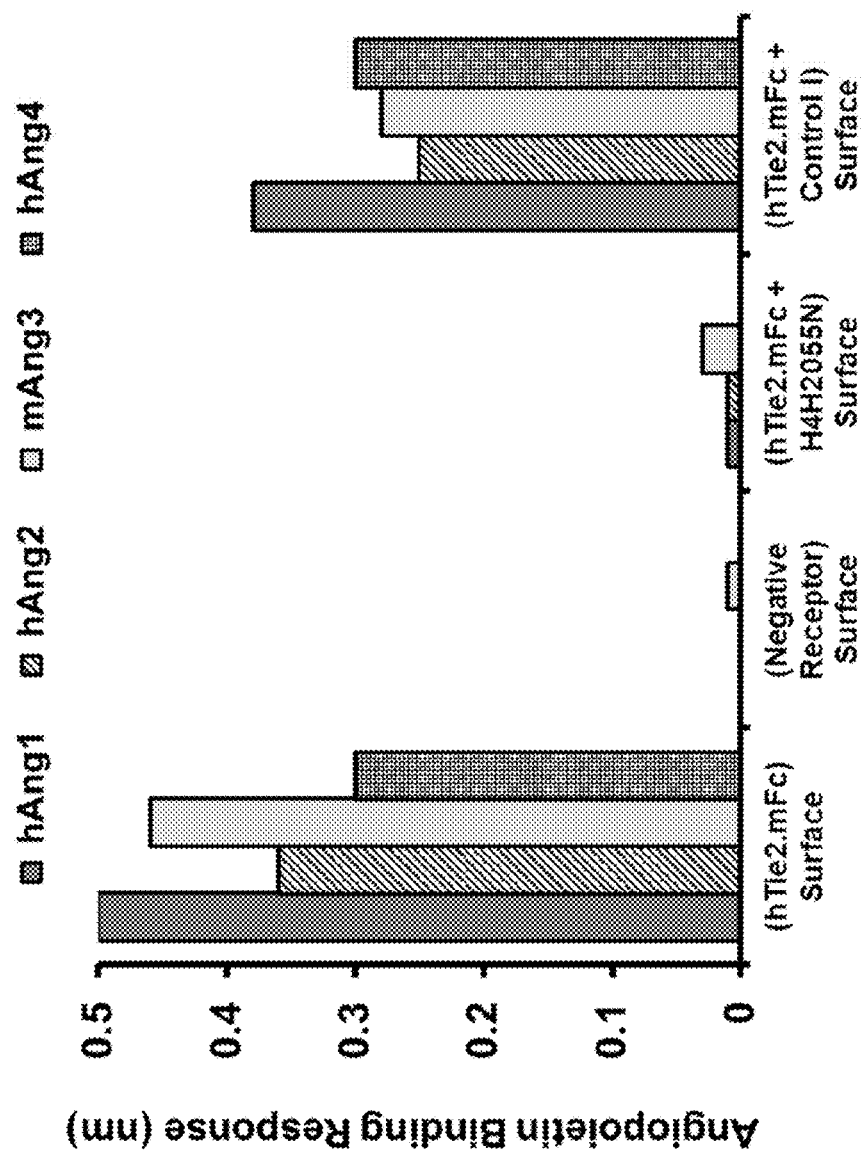
FIG. 2. Histogram showing the extent of angiopoietin (hAng1, hAng2, mAng3 or hAng4) binding to a hTie2-coated sensor tip pre-treated with anti-Tie2 antibody H4H2055N or Control I.

A further set of experiments was conducted to evaluate the ability of H4H2055N to block Tie2 binding to Ang2 and other members of the angiopoietin family (Ang1, Ang3 and Ang4). In this set of experiments, an Octet Red biosensor was employed using two experimental formats. In the first format, hTie2.mFc (SEQ ID NO:4; 10 μg/ml) or a negative control was captured on anti-mFc Octet senor tips for 5 min. The captured sensor tip surfaces were then saturated with H4H2055N or Control I antibody by dipping into wells containing 300 nM of respective monoclonal antibodies for 10 min. Finally the sensor tips were placed into wells containing 100 nM of hAng1 (R&D Systems, Inc., Minneapolis, Minn., Cat 923-AN/CF; Accession #Q5HYA0), hAng2 (R&D Systems, Inc., Minneapolis, Minn., Cat 623-AN/CF; Accession #O15123), mAng3 (R&D Systems, Inc., Minneapolis, Minn., Cat 738-AN/CF; Accession #Q9WVH6) or hAng4 (R&D Systems, Inc., Minneapolis, Minn., Cat 964-AN/CF; Accession Q9Y264) for 5 min. Binding response at each step of the experiment was monitored and the binding of different angiopoietins to the monoclonal antibody saturated receptor surfaces was plotted (FIG. 2). As illustrated by FIG. 2, H4H2055N blocked the binding of all four angiopoietins to the hTie2.mFc surface. The Control I antibody did not block binding of any of the angiopoietins to the Tie2-coated surfaces.

Figure 3:
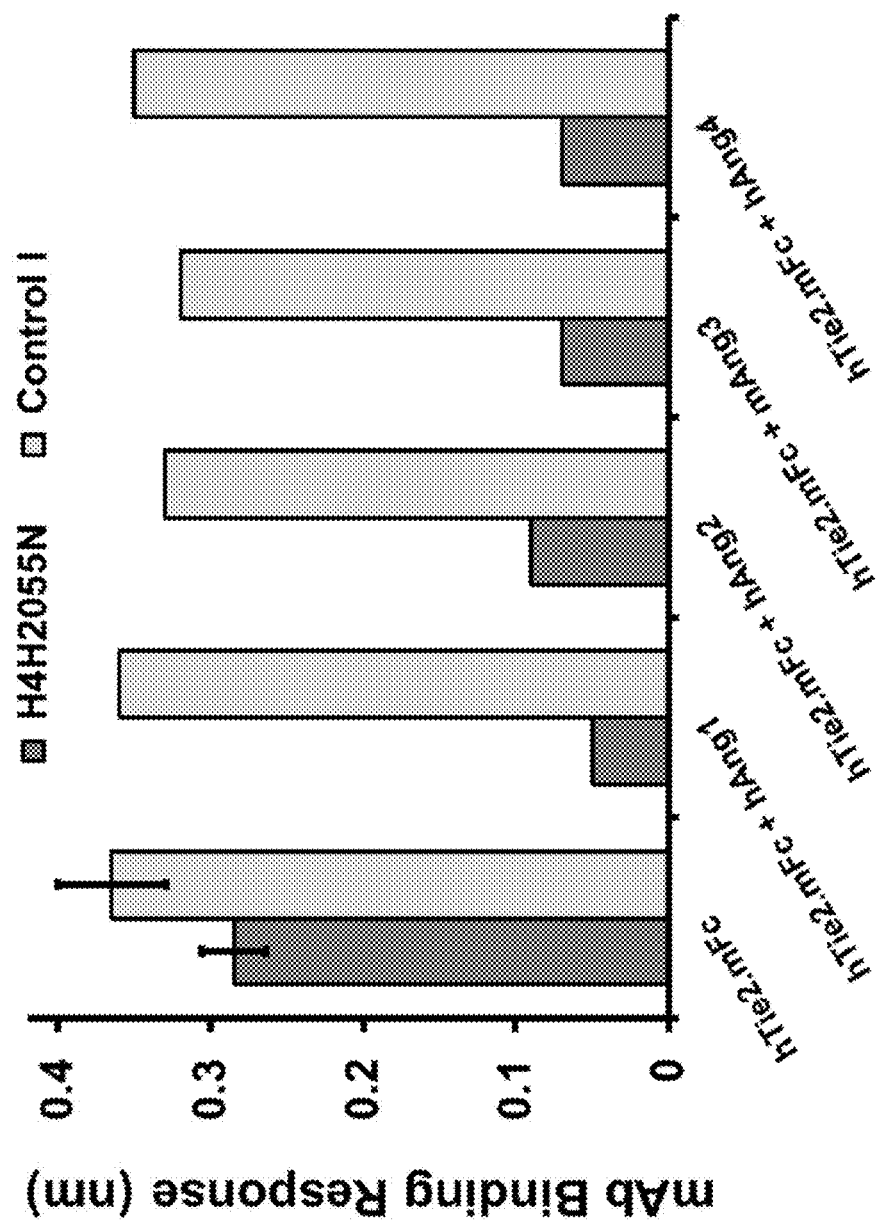
FIG. 3. Histogram showing the extent of anti-Tie2 antibody (H4H2055N or Control I) binding to a hTie2-coated sensor tip pre-treated with 100 nM of angiopoietin (hAng1, hAng2, mAng3 or hAng4).
Figure 4:
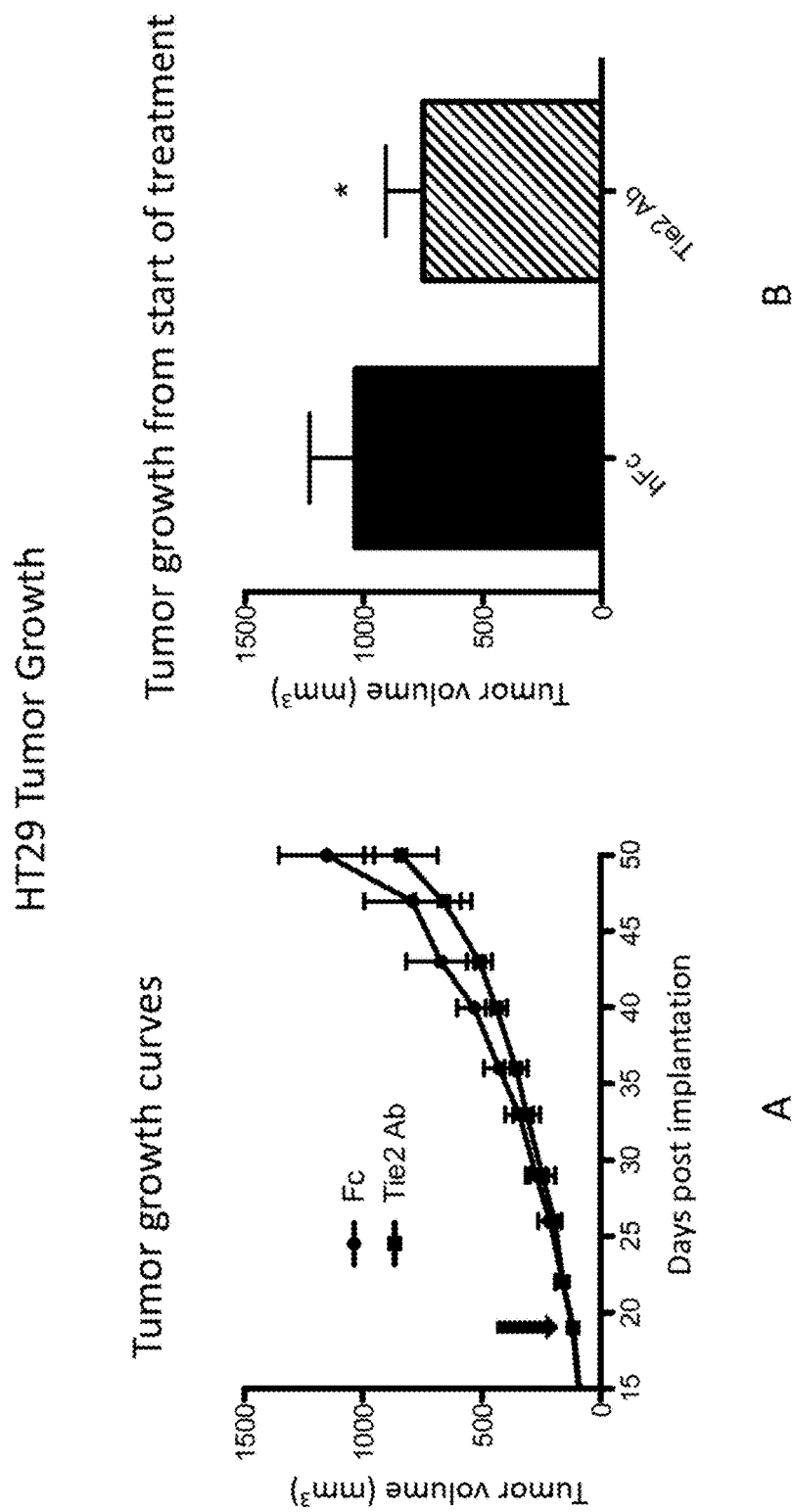
FIG. 4. Panel A shows the H29 tumor growth curves in mice following administration of anti-Tie2 antibody H2M2055N (■) or Fc control (●). Downward arrow indicates the treatment start date. Panel B shows the tumor growth from the start of treatment in mice treated with anti-Tie2 antibody H2M2055N or Fc control. Asterisk (*) indicates p<0.05 Mann Whitney non-parametric two-tailed t-test.
Figure 5:
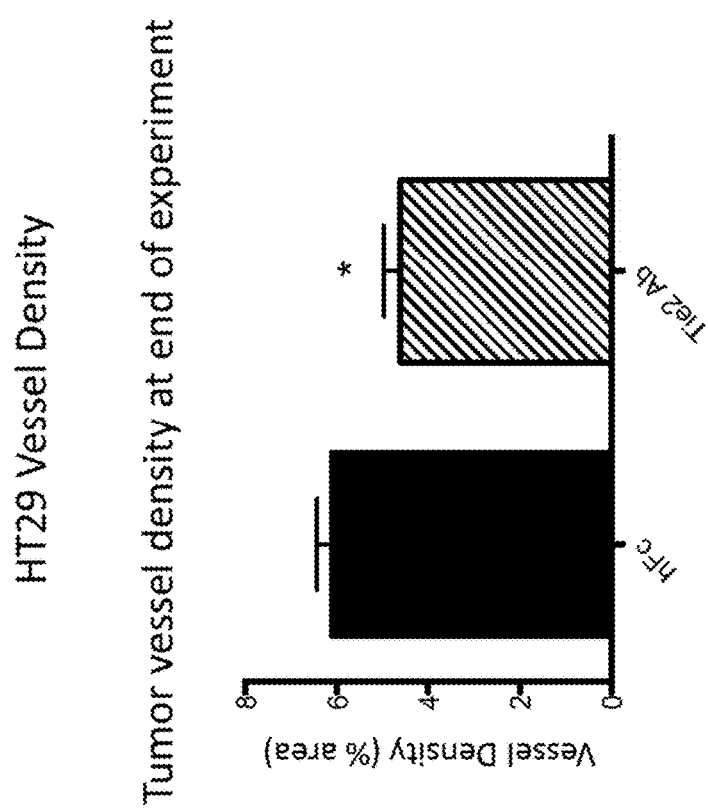
FIG. 5. H29 tumor vessel density measured at the end of the experiment in mice treated with anti-Tie2 antibody H2M2055N or Fc control. Asterisk (*) indicates p<0.05 Mann Whitney non-parametric two-tailed t-test.
Figure 6:
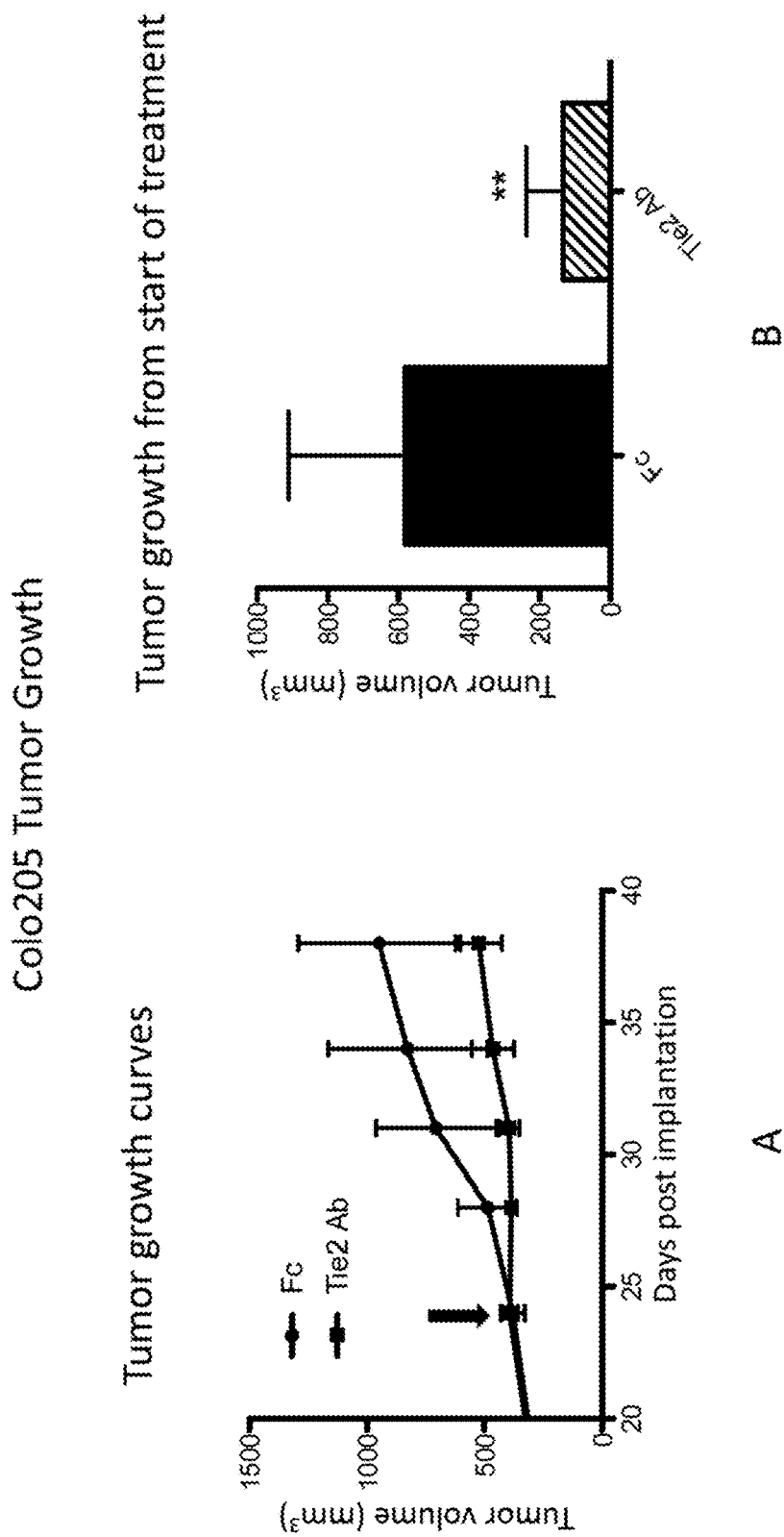
FIG. 6. Panel A shows the Colo305 tumor growth curves in mice following administration of anti-Tie2 antibody H2M2055N (■) or Fc control (●). Downward arrow indicates the treatment start date. Panel B shows the tumor growth from the start of treatment in mice treated with anti-Tie2 antibody H2M2055N or Fc control. Asterisk (*) indicates p<0.05 Mann Whitney non-parametric two-tailed t-test.
Figure 7:
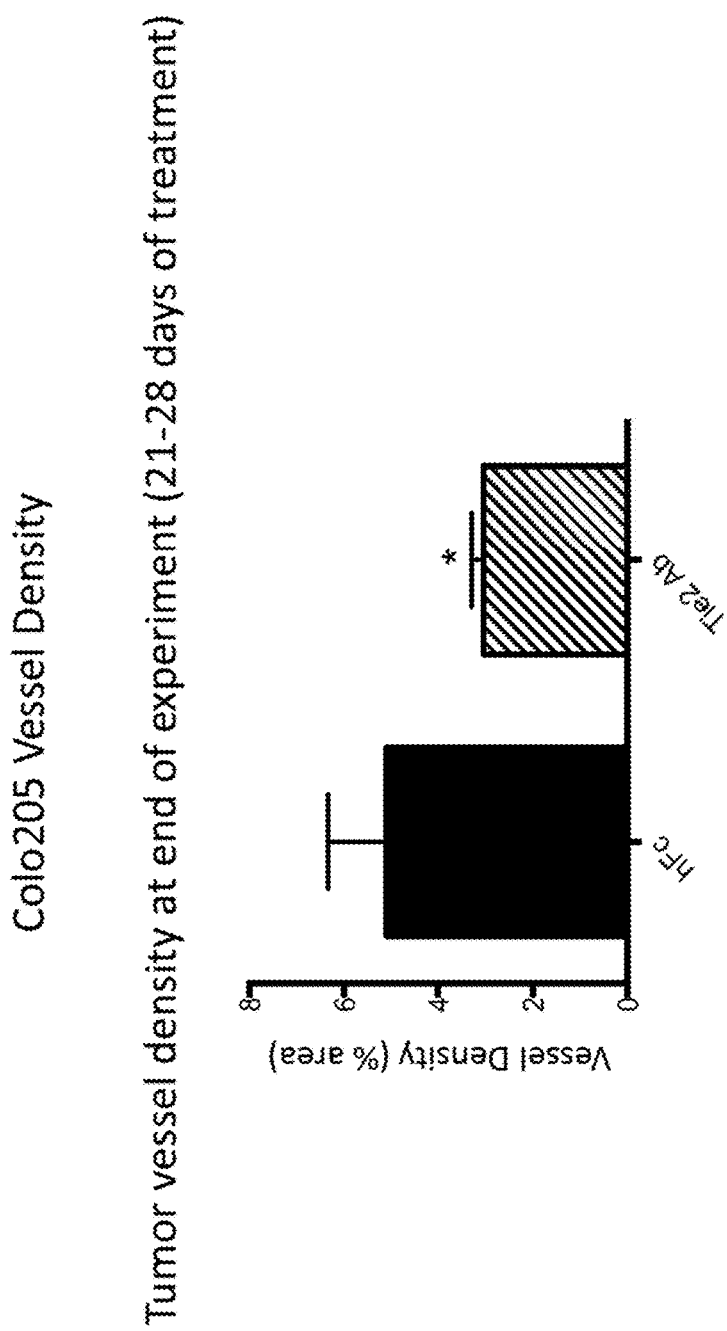
FIG. 7. Colo205 tumor vessel density measured at the end of the experiment in mice treated with anti-Tie2 antibody H2M2055N or Fc control. Asterisk (*) indicates p<0.05 Mann Whitney non-parametric two-tailed t-test.

In the second assay format, hTie2.mFc (10 μg/ml) or negative control was captured on anti-mFc coated Octet sensor tips (5 min), followed by placing the tips into different wells containing 100 nM of angiopoietin (hAng1, hAng2, mAng3 or hAng4) for 10 min. Lastly, the senor tips were placed into wells containing 300 nM of H4H2055N or Control I (5 min). As in format 1, the binding response at each step was monitored and the binding response was plotted (FIG. 3). This format demonstrated that, unlike Control I, the binding of H4H2055N is diminished by the already bound angiopoietins on the Tie2-coated surfaces. Thus, H4H2055N competes with the angiopoietins (Ang1, Ang2, Ang3 and Ang4) for binding to Tie2.

Example 6

Assessment of the Ability of Anti-Tie2 Antibodies to Block Angiopoietin-Mediated Tie2 Signaling To further characterize anti-hTie2 mAbs of the invention, the ability of the antibodies to block Tie2-induced luciferase activity was explored. Briefly, HEK293 cells were stably transfected with hTie2, and the top 10% of Tie2 expressing cells were isolated via FACS. These cells were then transduced with a serum response element (SRE)-dependent luciferase reporter lentivirus (SA Biosciences), and a clonal population (293-TIE2/SRE-Luc) with robust response to tetrameric forms of angiopoietin-1 (Bow-Ang1, SEQ ID NO:14) and angiopoietin-2 (Bow-Ang2, SEQ ID NO:13) was isolated.

For assays, 293-Tie2/SRE-Luc cells were seeded (30,000 cells per well) in 96-well plates one day prior to treatment. Dose-response curves were generated with serial dilutions of Bow-Ang1 (BA1) or Bow-Ang2 (BA2) incubated with cells for 4 h before measurement of luciferase activity. For Tie2 inhibition, cells were treated with serially diluted Tie2 mAbs in the presence of a 1 nM constant dose of BA1 or BA2 for 4 h. Luciferase activity was measured on a Victor luminometer following incubation with One-Glo™ (Promega) reagent. Three classes of antibodies were observed: Blockers, defined as a reduction in Tie2 dependent luciferase activity upon addition of antibody; Activators, defined as an increase in Tie2 dependent luciferase activity upon addition of antibody; and Not Active, defined as no significant change in signal upon their addition. For "Not Active" antibodies, no $EC_{50}$ or $IC_{50}$ value was calculated. Results are summarized in Table 8.

TABLE 8

$IC_{50}$ values for Anti-Tie2 antibodies

| Antibody | Mab Class (BowAng1) | $EC_{50}$ or $IC_{50}$ ± SEM ($10^{-9}$ M) BowAng1 | Mab Class (BowAng2) | $EC_{50}$ or $IC_{50}$ ± SEM ($10^{-9}$ M) BowAng2 |
|---|---|---|---|---|
| H2aM2760N | Blocker | 11.6 ± .81 | Blocker | 2.8 ± .14 |
| H2aM2761N | Blocker, not to baseline | 5.2 ± 1.3 | Blocker, not to baseline | 1.1 ± .11 |
| H4H2055N | Blocker | 0.69 ± .16 | Blocker | 0.23 ± .03 |
| H1H2304B | No activity | NA | No activity | NA |
| H1H2317B | No activity | NA | No activity | NA |
| H1H2322B | No activity | NA | No activity | NA |
| H1H2324B | No activity | NA | No activity | NA |
| H1H2331B | Activator | 13.6 ± 3.1 | Activator | 5.1 ± 1.9 |
| H1H2332B | Activator | 2.5 ± 1.2 | Activator | 3.7 ± .15 |
| H1H2333B | No activity | NA | No activity | NA |
| H1H2337B | Activator | 1.1 ± .02 | Activator | 4.7 ± .80 |
| H1H2338B | No activity | NA | No activity | NA |
| H1H2339B | Activator | 10.3 ± .23 | Activator | 13.0 ± 3.5 |
| H1H2340B | Activator | 1.41 ± .01 | Activator | 2.1 ± .04 |
| Control I | Activator | 0.76 ± .50 | Activator | 1.4 ± .03 |

$IC_{50}$ values are reported for Blockers, and $EC_{50}$ values are reported for Activators Anti-Tie2 antibodies H2aM2760N, H2aM2761N and H4H2055N were identified as blockers in this experimental system.

Example 7

Assessment of the Anti-Tumor Activity of an Anti-Tie2 Antibody in vivo

An exemplary anti-Tie2 antibody (H2M2055N) was tested for its ability to inhibit the growth of human tumor xenografts in immunocompromised mice. Briefly, either human colorectal HT29 or Colo205 tumors were grown in SCID mice. When tumors were palpable (100 mm$^3$ for HT29 and 400 mm$^3$ for Colo205) animals were treated biweekly with Fc protein (10 mg/kg) or anti-Tie2 antibody (H1M2055N; 10 mg/kg). At the end of treatment (31 days for HT29 & 14 days for Colo205), the percent tumor growth inhibition (% TGI) was determined (Table 9) and tumor tissue was harvested and utilized for vessel density analysis. Vascular density was assessed in 30 μm thick OCT tumor sections by CD31 immunohistochemistry. NIH Image software was utilized to determine the % area vessel density in the tumor tissue sections. Results are illustrated graphically in FIGS. 4-7.

TABLE 9

Percent Decrease in Tumor Growth with Anti-Tie2 Mab Treatment

| | HT29 | | Colo205 | |
|---|---|---|---|---|
| Antibody | Avg Tumor Growth (mm3) from start of treatment | % Decrease in Tumor Growth | Avg Tumor Growth (mm3) from start of treatment | % Decrease in Tumor Growth |
| Fc protein (10 mg/kg) | 100 | | 400 | |
| H2M2055N (10 mg/kg) | 100 | 27.5 | 400 | 77 |

As shown in this Example, the anti-Tie2 Ab, H1M2055N, not only decreased tumor growth (Table 9), but also significantly decreased vessel density in both HT29 (25%, FIG. 5) and Colo205 (40%, FIG. 7) xenograft models.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated antibody or antigen-binding fragment thereof that specifically binds human Tie2, comprising the complementarity determining regions (CDRs), HCDR1, HCDR2, HCDR3, LCDR1, LCDR2 and LCDR3, of an antibody produced from a cell line deposited with the American Type Culture Collection under accession number PTA-12296.

2. The isolated antibody or antigen-binding fragment of claim 1, comprising the variable regions of an antibody produced from a cell line deposited with the American Type Culture Collection under accession number PTA-12296.

3. The isolated antibody or antigen-binding fragment of claim 1 that is an antibody.

4. The isolated antibody of claim 3 that is an IgG1 antibody.

5. The isolated antibody of claim 3 that is an IgG4 antibody.

6. The isolated antibody or antigen-binding fragment of claim 1 that is an antigen-binding fragment.

7. The isolated antibody or antigen-binding fragment of claim 1 that is multispecific.

* * * * *

SEQUENCE LISTING

```
<160> NUMBER OF SEQ ID NOS: 18

<210> SEQ ID NO 1
<211> LENGTH: 1124
<212> TYPE: PRT
<213> ORGANISM: Homo sapiens

<400> SEQUENCE: 1

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205
```

-continued

```
Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
                260                 265                 270

Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
                340                 345                 350

Val Asp Leu Pro Asp His Ile Glu Val Asn Ser Gly Lys Phe Asn Pro
                355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
                420                 425                 430

Val Glu Lys Pro Phe Asn Ile Ser Val Lys Val Leu Pro Lys Pro Leu
                435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
                500                 505                 510

Tyr Glu Leu Cys Val Gln Leu Val Arg Arg Gly Glu Gly Gly Glu Gly
            515                 520                 525

His Pro Gly Pro Val Arg Arg Phe Thr Thr Ala Ser Ile Gly Leu Pro
530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
                580                 585                 590

Val Pro Gly Asn Leu Thr Ser Val Leu Leu Asn Asn Leu His Pro Arg
            595                 600                 605

Glu Gln Tyr Val Val Arg Ala Arg Val Asn Thr Lys Ala Gln Gly Glu
            610                 615                 620
```

```
Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
            645                 650                 655

Ile Ser Trp Thr Ile Leu Asp Gly Tyr Ser Ile Ser Ser Ile Thr Ile
                660                 665                 670

Arg Tyr Lys Val Gln Gly Lys Asn Glu Asp Gln His Val Asp Val Lys
            675                 680                 685

Ile Lys Asn Ala Thr Ile Thr Gln Tyr Gln Leu Lys Gly Leu Glu Pro
690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
                740                 745                 750

Gly Ser Ala Gly Met Thr Cys Leu Thr Val Leu Leu Ala Phe Leu Ile
                755                 760                 765

Ile Leu Gln Leu Lys Arg Ala Asn Val Gln Arg Arg Met Ala Gln Ala
770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
                820                 825                 830

Gly Asn Phe Gly Gln Val Leu Lys Ala Arg Ile Lys Lys Asp Gly Leu
                835                 840                 845

Arg Met Asp Ala Ala Ile Lys Arg Met Lys Glu Tyr Ala Ser Lys Asp
850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
                900                 905                 910

Phe Leu Arg Lys Ser Arg Val Leu Glu Thr Asp Pro Ala Phe Ala Ile
                915                 920                 925

Ala Asn Ser Thr Ala Ser Thr Leu Ser Ser His His Leu Leu His Phe
930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
                980                 985                 990

Val Lys Lys Thr Met Gly Arg Leu Pro Val Arg Trp Met Ala Ile Glu
                995                 1000                1005

Ser Leu Asn Tyr Ser Val Tyr Thr Thr Asn Ser Asp Val Trp Ser Tyr
        1010                1015                1020

Gly Val Leu Leu Trp Glu Ile Val Ser Leu Gly Gly Thr Pro Tyr Cys
1025                1030                1035                1040
```

Gly Met Thr Cys Ala Glu Leu Tyr Glu Lys Leu Pro Gln Gly Tyr Arg
            1045                1050                1055

Leu Glu Lys Pro Leu Asn Cys Asp Asp Glu Val Tyr Asp Leu Met Arg
            1060                1065                1070

Gln Cys Trp Arg Glu Lys Pro Tyr Glu Arg Pro Ser Phe Ala Gln Ile
            1075                1080                1085

Leu Val Ser Leu Asn Arg Met Leu Glu Glu Arg Lys Thr Tyr Val Asn
            1090                1095                1100

Thr Thr Leu Tyr Glu Lys Phe Thr Tyr Ala Gly Ile Asp Cys Ser Ala
1105                1110                1115                1120

Glu Glu Ala Ala

<210> SEQ ID NO 2
<211> LENGTH: 735
<212> TYPE: PRT
<213> ORGANISM: Artificial Sequence
<220> FEATURE:
<223> OTHER INFORMATION: Synthetic

<400> SEQUENCE: 2

Thr Val Glu Gly Ala Met Asp Leu Ile Leu Ile Asn Ser Leu Pro Leu
1               5                   10                  15

Val Ser Asp Ala Glu Thr Ser Leu Thr Cys Ile Ala Ser Gly Trp Arg
            20                  25                  30

Pro His Glu Pro Ile Thr Ile Gly Arg Asp Phe Glu Ala Leu Met Asn
            35                  40                  45

Gln His Gln Asp Pro Leu Glu Val Thr Gln Asp Val Thr Arg Glu Trp
        50                  55                  60

Ala Lys Lys Val Val Trp Lys Arg Glu Lys Ala Ser Lys Ile Asn Gly
65                  70                  75                  80

Ala Tyr Phe Cys Glu Gly Arg Val Arg Gly Glu Ala Ile Arg Ile Arg
                85                  90                  95

Thr Met Lys Met Arg Gln Gln Ala Ser Phe Leu Pro Ala Thr Leu Thr
            100                 105                 110

Met Thr Val Asp Lys Gly Asp Asn Val Asn Ile Ser Phe Lys Lys Val
            115                 120                 125

Leu Ile Lys Glu Glu Asp Ala Val Ile Tyr Lys Asn Gly Ser Phe Ile
        130                 135                 140

His Ser Val Pro Arg His Glu Val Pro Asp Ile Leu Glu Val His Leu
145                 150                 155                 160

Pro His Ala Gln Pro Gln Asp Ala Gly Val Tyr Ser Ala Arg Tyr Ile
                165                 170                 175

Gly Gly Asn Leu Phe Thr Ser Ala Phe Thr Arg Leu Ile Val Arg Arg
            180                 185                 190

Cys Glu Ala Gln Lys Trp Gly Pro Glu Cys Asn His Leu Cys Thr Ala
            195                 200                 205

Cys Met Asn Asn Gly Val Cys His Glu Asp Thr Gly Glu Cys Ile Cys
        210                 215                 220

Pro Pro Gly Phe Met Gly Arg Thr Cys Glu Lys Ala Cys Glu Leu His
225                 230                 235                 240

Thr Phe Gly Arg Thr Cys Lys Glu Arg Cys Ser Gly Gln Glu Gly Cys
                245                 250                 255

Lys Ser Tyr Val Phe Cys Leu Pro Asp Pro Tyr Gly Cys Ser Cys Ala
            260                 265                 270

```
Thr Gly Trp Lys Gly Leu Gln Cys Asn Glu Ala Cys His Pro Gly Phe
            275                 280                 285

Tyr Gly Pro Asp Cys Lys Leu Arg Cys Ser Cys Asn Asn Gly Glu Met
        290                 295                 300

Cys Asp Arg Phe Gln Gly Cys Leu Cys Ser Pro Gly Trp Gln Gly Leu
305                 310                 315                 320

Gln Cys Glu Arg Glu Gly Ile Pro Arg Met Thr Pro Lys Ile Val Asp
                325                 330                 335

Leu Pro Asp His Ile Glu Val Asn Ser Gly Lys Phe Asn Pro Ile Cys
            340                 345                 350

Lys Ala Ser Gly Trp Pro Leu Pro Thr Asn Glu Glu Met Thr Leu Val
        355                 360                 365

Lys Pro Asp Gly Thr Val Leu His Pro Lys Asp Phe Asn His Thr Asp
370                 375                 380

His Phe Ser Val Ala Ile Phe Thr Ile His Arg Ile Leu Pro Pro Asp
385                 390                 395                 400

Ser Gly Val Trp Val Cys Ser Val Asn Thr Val Ala Gly Met Val Glu
                405                 410                 415

Lys Pro Phe Asn Ile Ser Val Lys Val Leu Pro Lys Pro Leu Asn Ala
            420                 425                 430

Pro Asn Val Ile Asp Thr Gly His Asn Phe Ala Val Ile Asn Ile Ser
        435                 440                 445

Ser Glu Pro Tyr Phe Gly Asp Gly Pro Ile Lys Ser Lys Lys Leu Leu
    450                 455                 460

Tyr Lys Pro Val Asn His Tyr Glu Ala Trp Gln His Ile Gln Val Thr
465                 470                 475                 480

Asn Glu Ile Val Thr Leu Asn Tyr Leu Glu Pro Arg Thr Glu Tyr Glu
                485                 490                 495

Leu Cys Val Gln Leu Val Arg Arg Gly Glu Gly Gly Glu Gly His Pro
            500                 505                 510

Gly Pro Val Arg Arg Phe Thr Thr Ala Ser Ile Gly Leu Pro Pro Pro
        515                 520                 525

Arg Gly Leu Asn Leu Leu Pro Lys Ser Gln Thr Thr Leu Asn Leu Thr
    530                 535                 540

Trp Gln Pro Ile Phe Pro Ser Ser Glu Asp Asp Phe Tyr Val Glu Val
545                 550                 555                 560

Glu Arg Arg Ser Val Gln Lys Ser Asp Gln Gln Asn Ile Lys Val Pro
                565                 570                 575

Gly Asn Leu Thr Ser Val Leu Leu Asn Asn Leu His Pro Arg Glu Gln
            580                 585                 590

Tyr Val Val Arg Ala Arg Val Asn Thr Lys Ala Gln Gly Glu Trp Ser
        595                 600                 605

Glu Asp Leu Thr Ala Trp Thr Leu Ser Asp Ile Leu Pro Pro Gln Pro
    610                 615                 620

Glu Asn Ile Lys Ile Ser Asn Ile Thr His Ser Ser Ala Val Ile Ser
625                 630                 635                 640

Trp Thr Ile Leu Asp Gly Tyr Ser Ile Ser Ile Thr Ile Arg Tyr
                645                 650                 655

Lys Val Gln Gly Lys Asn Glu Asp Gln His Val Asp Val Lys Ile Lys
            660                 665                 670

Asn Ala Thr Ile Thr Gln Tyr Gln Leu Lys Gly Leu Glu Pro Glu Thr
        675                 680                 685
```

```
Ala Tyr Gln Val Asp Ile Phe Ala Glu Asn Asn Ile Gly Ser Ser Asn
    690             695                 700

Pro Ala Phe Ser His Glu Leu Val Thr Leu Pro Glu Ser Gln Ala Pro
705             710                 715                 720

Ala Asp Leu Gly Gly Gly Lys Ile Asp His His His His His
            725             730                 735

<210> SEQ ID NO 3
<211> LENGTH: 958
<212> TYPE: PRT
<213> ORGANISM: Artificial Sequence
<220> FEATURE:
<223> OTHER INFORMATION: Synthetic

<400> SEQUENCE: 3

Ala Met Asp Leu Ile Leu Ile Asn Ser Leu Pro Leu Val Ser Asp Ala
1               5                   10                  15

Glu Thr Ser Leu Thr Cys Ile Ala Ser Gly Trp Arg Pro His Glu Pro
            20                  25                  30

Ile Thr Ile Gly Arg Asp Phe Glu Ala Leu Met Asn Gln His Gln Asp
        35                  40                  45

Pro Leu Glu Val Thr Gln Asp Val Thr Arg Glu Trp Ala Lys Lys Val
    50                  55                  60

Val Trp Lys Arg Glu Lys Ala Ser Lys Ile Asn Gly Ala Tyr Phe Cys
65              70                  75                  80

Glu Gly Arg Val Arg Gly Glu Ala Ile Arg Ile Arg Thr Met Lys Met
                85                  90                  95

Arg Gln Gln Ala Ser Phe Leu Pro Ala Thr Leu Thr Met Thr Val Asp
            100                 105                 110

Lys Gly Asp Asn Val Asn Ile Ser Phe Lys Lys Val Leu Ile Lys Glu
        115                 120                 125

Glu Asp Ala Val Ile Tyr Lys Asn Gly Ser Phe Ile His Ser Val Pro
    130                 135                 140

Arg His Glu Val Pro Asp Ile Leu Glu Val His Leu Pro His Ala Gln
145             150                 155                 160

Pro Gln Asp Ala Gly Val Tyr Ser Ala Arg Tyr Ile Gly Gly Asn Leu
                165                 170                 175

Phe Thr Ser Ala Phe Thr Arg Leu Ile Val Arg Arg Cys Glu Ala Gln
            180                 185                 190

Lys Trp Gly Pro Glu Cys Asn His Leu Cys Thr Ala Cys Met Asn Asn
        195                 200                 205

Gly Val Cys His Glu Asp Thr Gly Glu Cys Ile Cys Pro Pro Gly Phe
    210                 215                 220

Met Gly Arg Thr Cys Glu Lys Ala Cys Glu Leu His Thr Phe Gly Arg
225             230                 235                 240

Thr Cys Lys Glu Arg Cys Ser Gly Gln Glu Gly Cys Lys Ser Tyr Val
                245                 250                 255

Phe Cys Leu Pro Asp Pro Tyr Gly Cys Ser Cys Ala Thr Gly Trp Lys
            260                 265                 270

Gly Leu Gln Cys Asn Glu Ala Cys His Pro Gly Phe Tyr Gly Pro Asp
        275                 280                 285

Cys Lys Leu Arg Cys Ser Cys Asn Asn Gly Glu Met Cys Asp Arg Phe
    290                 295                 300

Gln Gly Cys Leu Cys Ser Pro Gly Trp Gln Gly Leu Gln Cys Glu Arg
305             310                 315                 320
```

-continued

Glu Gly Ile Gln Arg Met Thr Pro Lys Ile Val Asp Leu Pro Asp His
                    325                 330                 335

Ile Glu Val Asn Ser Gly Lys Phe Asn Pro Ile Cys Lys Ala Ser Gly
            340                 345                 350

Trp Pro Leu Pro Thr Asn Glu Glu Met Thr Leu Val Lys Pro Asp Gly
                355                 360                 365

Thr Val Leu His Pro Lys Asp Phe Asn His Thr Asp His Phe Ser Val
        370                 375                 380

Ala Ile Phe Thr Ile His Arg Ile Leu Pro Pro Asp Ser Gly Val Trp
385                 390                 395                 400

Val Cys Ser Val Asn Thr Val Ala Gly Met Val Glu Lys Pro Phe Asn
                405                 410                 415

Ile Ser Val Lys Val Leu Pro Lys Pro Leu Asn Ala Pro Asn Val Ile
                420                 425                 430

Asp Thr Gly His Asn Phe Ala Val Ile Asn Ile Ser Ser Glu Pro Tyr
                435                 440                 445

Phe Gly Asp Gly Pro Ile Lys Ser Lys Lys Leu Leu Tyr Lys Pro Val
        450                 455                 460

Asn His Tyr Glu Ala Trp Gln His Ile Gln Val Thr Asn Glu Ile Val
465                 470                 475                 480

Thr Leu Asn Tyr Leu Glu Pro Arg Thr Glu Tyr Glu Leu Cys Val Gln
                485                 490                 495

Leu Val Arg Arg Gly Glu Gly Gly Glu Gly His Pro Gly Pro Val Arg
        500                 505                 510

Arg Phe Thr Thr Ala Ser Ile Gly Leu Pro Pro Arg Gly Leu Asn
                515                 520                 525

Leu Leu Pro Lys Ser Gln Thr Thr Leu Asn Leu Thr Trp Gln Pro Ile
        530                 535                 540

Phe Pro Ser Ser Glu Asp Asp Phe Tyr Val Glu Val Glu Arg Arg Ser
545                 550                 555                 560

Val Gln Lys Ser Asp Gln Gln Asn Ile Lys Val Pro Gly Asn Leu Thr
                565                 570                 575

Ser Val Leu Leu Asn Asn Leu His Pro Arg Glu Gln Tyr Val Val Arg
                580                 585                 590

Ala Arg Val Asn Thr Lys Ala Gln Gly Glu Trp Ser Glu Asp Leu Thr
        595                 600                 605

Ala Trp Thr Leu Ser Asp Ile Leu Pro Pro Gln Pro Glu Asn Ile Lys
        610                 615                 620

Ile Ser Asn Ile Thr His Ser Ser Ala Val Ile Ser Trp Thr Ile Leu
625                 630                 635                 640

Asp Gly Tyr Ser Ile Ser Ser Ile Thr Ile Arg Tyr Lys Val Gln Gly
                645                 650                 655

Lys Asn Glu Asp Gln His Val Asp Val Lys Ile Lys Asn Ala Thr Ile
                660                 665                 670

Thr Gln Tyr Gln Leu Lys Gly Leu Glu Pro Glu Thr Ala Tyr Gln Val
        675                 680                 685

Asp Ile Phe Ala Glu Asn Asn Ile Gly Ser Ser Asn Pro Ala Phe Ser
        690                 695                 700

His Glu Leu Val Thr Leu Pro Glu Ser Gln Ala Pro Ala Asp Leu Gly
705                 710                 715                 720

Gly Gly Lys Gly Pro Gly Glu Pro Lys Ser Cys Asp Lys Thr His Thr
                725                 730                 735

Cys Pro Pro Cys Pro Ala Pro Glu Leu Leu Gly Gly Pro Ser Val Phe

```
                    740                 745                 750
Leu Phe Pro Pro Lys Pro Lys Asp Thr Leu Met Ile Ser Arg Thr Pro
                755                 760                 765

Glu Val Thr Cys Val Val Val Asp Val Ser His Glu Asp Pro Glu Val
            770                 775                 780

Lys Phe Asn Trp Tyr Val Asp Gly Val Glu Val His Asn Ala Lys Thr
785                 790                 795                 800

Lys Pro Arg Glu Glu Gln Tyr Asn Ser Thr Tyr Arg Val Val Ser Val
                805                 810                 815

Leu Thr Val Leu His Gln Asp Trp Leu Asn Gly Lys Glu Tyr Lys Cys
            820                 825                 830

Lys Val Ser Asn Lys Ala Leu Pro Ala Pro Ile Glu Lys Thr Ile Ser
        835                 840                 845

Lys Ala Lys Gly Gln Pro Arg Glu Pro Gln Val Tyr Thr Leu Pro Pro
    850                 855                 860

Ser Arg Asp Glu Leu Thr Lys Asn Gln Val Ser Leu Thr Cys Leu Val
865                 870                 875                 880

Lys Gly Phe Tyr Pro Ser Asp Ile Ala Val Glu Trp Glu Ser Asn Gly
                885                 890                 895

Gln Pro Glu Asn Asn Tyr Lys Thr Thr Pro Pro Val Leu Asp Ser Asp
            900                 905                 910

Gly Ser Phe Phe Leu Tyr Ser Lys Leu Thr Val Asp Lys Ser Arg Trp
        915                 920                 925

Gln Gln Gly Asn Val Phe Ser Cys Ser Val Met His Glu Ala Leu His
    930                 935                 940

Asn His Tyr Thr Gln Lys Ser Leu Ser Leu Ser Pro Gly Lys
945                 950                 955

<210> SEQ ID NO 4
<211> LENGTH: 981
<212> TYPE: PRT
<213> ORGANISM: Artificial Sequence
<220> FEATURE:
<223> OTHER INFORMATION: Synthetic

<400> SEQUENCE: 4

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
```

-continued

```
            145                 150                 155                 160
        Phe Ile His Ser Val Pro Arg His Glu Val Pro Asp Ile Leu Glu Val
                        165                 170                 175
        His Leu Pro His Ala Gln Pro Gln Asp Ala Gly Val Tyr Ser Ala Arg
                        180                 185                 190
        Tyr Ile Gly Gly Asn Leu Phe Thr Ser Ala Phe Thr Arg Leu Ile Val
                        195                 200                 205
        Arg Arg Cys Glu Ala Gln Lys Trp Gly Pro Glu Cys Asn His Leu Cys
        210                 215                 220
        Thr Ala Cys Met Asn Asn Gly Val Cys His Glu Asp Thr Gly Glu Cys
        225                 230                 235                 240
        Ile Cys Pro Pro Gly Phe Met Gly Arg Thr Cys Glu Lys Ala Cys Glu
                        245                 250                 255
        Leu His Thr Phe Gly Arg Thr Cys Lys Glu Arg Cys Ser Gly Gln Glu
                        260                 265                 270
        Gly Cys Lys Ser Tyr Val Phe Cys Leu Pro Asp Pro Tyr Gly Cys Ser
                        275                 280                 285
        Cys Ala Thr Gly Trp Lys Gly Leu Gln Cys Asn Glu Ala Cys His Pro
        290                 295                 300
        Gly Phe Tyr Gly Pro Asp Cys Lys Leu Arg Cys Ser Cys Asn Asn Gly
        305                 310                 315                 320
        Glu Met Cys Asp Arg Phe Gln Gly Cys Leu Cys Ser Pro Gly Trp Gln
                        325                 330                 335
        Gly Leu Gln Cys Glu Arg Glu Gly Ile Pro Arg Met Thr Pro Lys Ile
                        340                 345                 350
        Val Asp Leu Pro Asp His Ile Glu Val Asn Ser Gly Lys Phe Asn Pro
                        355                 360                 365
        Ile Cys Lys Ala Ser Gly Trp Pro Leu Pro Thr Asn Glu Glu Met Thr
                        370                 375                 380
        Leu Val Lys Pro Asp Gly Thr Val Leu His Pro Lys Asp Phe Asn His
        385                 390                 395                 400
        Thr Asp His Phe Ser Val Ala Ile Phe Thr Ile His Arg Ile Leu Pro
                        405                 410                 415
        Pro Asp Ser Gly Val Trp Val Cys Ser Val Asn Thr Val Ala Gly Met
                        420                 425                 430
        Val Glu Lys Pro Phe Asn Ile Ser Val Lys Val Leu Pro Lys Pro Leu
                        435                 440                 445
        Asn Ala Pro Asn Val Ile Asp Thr Gly His Asn Phe Ala Val Ile Asn
        450                 455                 460
        Ile Ser Ser Glu Pro Tyr Phe Gly Asp Gly Pro Ile Lys Ser Lys Lys
        465                 470                 475                 480
        Leu Leu Tyr Lys Pro Val Asn His Tyr Glu Ala Trp Gln His Ile Gln
                        485                 490                 495
        Val Thr Asn Glu Ile Val Thr Leu Asn Tyr Leu Glu Pro Arg Thr Glu
                        500                 505                 510
        Tyr Glu Leu Cys Val Gln Leu Val Arg Arg Gly Glu Gly Gly Glu Gly
                        515                 520                 525
        His Pro Gly Pro Val Arg Arg Phe Thr Thr Ala Ser Ile Gly Leu Pro
                        530                 535                 540
        Pro Pro Arg Gly Leu Asn Leu Leu Pro Lys Ser Gln Thr Thr Leu Asn
        545                 550                 555                 560
        Leu Thr Trp Gln Pro Ile Phe Pro Ser Ser Glu Asp Asp Phe Tyr Val
                        565                 570                 575
```

```
Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Ile Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Gly Pro Gly Glu Pro Arg Gly
            740                 745                 750

Pro Thr Ile Lys Pro Cys Pro Pro Cys Lys Cys Pro Ala Pro Asn Leu
        755                 760                 765

Leu Gly Gly Pro Ser Val Phe Ile Phe Pro Pro Lys Ile Lys Asp Val
    770                 775                 780

Leu Met Ile Ser Leu Ser Pro Ile Val Thr Cys Val Val Asp Val
785                 790                 795                 800

Ser Glu Asp Asp Pro Asp Val Gln Ile Ser Trp Phe Val Asn Asn Val
                805                 810                 815

Glu Val His Thr Ala Gln Thr Gln Thr His Arg Glu Asp Tyr Asn Ser
            820                 825                 830

Thr Leu Arg Val Val Ser Ala Leu Pro Ile Gln His Gln Asp Trp Met
        835                 840                 845

Ser Gly Lys Glu Phe Lys Cys Lys Val Asn Asn Lys Asp Leu Pro Ala
    850                 855                 860

Pro Ile Glu Arg Thr Ile Ser Lys Pro Lys Gly Ser Val Arg Ala Pro
865                 870                 875                 880

Gln Val Tyr Val Leu Pro Pro Glu Glu Met Thr Lys Lys Gln
                885                 890                 895

Val Thr Leu Thr Cys Met Val Thr Asp Phe Met Pro Glu Asp Ile Tyr
            900                 905                 910

Val Glu Trp Thr Asn Asn Gly Lys Thr Glu Leu Asn Tyr Lys Asn Thr
        915                 920                 925

Glu Pro Val Leu Asp Ser Asp Gly Ser Tyr Phe Met Tyr Ser Lys Leu
    930                 935                 940

Arg Val Glu Lys Lys Asn Trp Val Glu Arg Asn Ser Tyr Ser Cys Ser
945                 950                 955                 960

Val Val His Glu Gly Leu His Asn His His Thr Thr Lys Ser Phe Ser
                965                 970                 975

Arg Thr Pro Gly Lys
            980
```

-continued

```
<210> SEQ ID NO 5
<211> LENGTH: 957
<212> TYPE: PRT
<213> ORGANISM: Artificial Sequence
<220> FEATURE:
<223> OTHER INFORMATION: Synthetic

<400> SEQUENCE: 5

Val Glu Gly Ala Met Asp Leu Ile Leu Ile Asn Ser Leu Pro Leu Val
1               5                   10                  15

Ser Asp Ala Glu Thr Ser Leu Thr Cys Ile Ala Ser Gly Trp His Pro
            20                  25                  30

His Glu Pro Ile Thr Ile Gly Arg Asp Phe Glu Ala Leu Met Asn Gln
        35                  40                  45

His Gln Asp Pro Leu Glu Val Thr Gln Asp Val Thr Arg Glu Trp Ala
    50                  55                  60

Lys Lys Val Val Trp Lys Arg Glu Lys Ala Ser Lys Ile Asn Gly Ala
65                  70                  75                  80

Tyr Phe Cys Glu Gly Arg Val Arg Gly Gln Ala Ile Arg Ile Arg Thr
                85                  90                  95

Met Lys Met Arg Gln Gln Ala Ser Phe Leu Pro Ala Thr Leu Thr Met
            100                 105                 110

Thr Val Asp Arg Gly Asp Asn Val Asn Ile Ser Phe Lys Lys Val Leu
        115                 120                 125

Ile Lys Glu Glu Asp Ala Val Ile Tyr Lys Asn Gly Ser Phe Ile His
    130                 135                 140

Ser Val Pro Arg His Glu Val Pro Asp Ile Leu Glu Val His Leu Pro
145                 150                 155                 160

His Ala Gln Pro Gln Asp Ala Gly Val Tyr Ser Ala Arg Tyr Ile Gly
                165                 170                 175

Gly Asn Leu Phe Thr Ser Ala Phe Thr Arg Leu Ile Val Arg Arg Cys
            180                 185                 190

Glu Ala Gln Lys Trp Gly Pro Asp Cys Asn Arg Pro Cys Thr Thr Cys
        195                 200                 205

Lys Asn Asn Gly Val Cys His Glu Asp Thr Gly Glu Cys Ile Cys Pro
    210                 215                 220

Pro Gly Phe Met Gly Arg Thr Cys Glu Lys Ala Cys Glu Pro His Thr
225                 230                 235                 240

Phe Gly Arg Thr Cys Lys Glu Arg Cys Ser Gly Ser Glu Gly Cys Lys
                245                 250                 255

Ser Tyr Val Phe Cys Leu Pro Asp Pro Tyr Gly Cys Ser Cys Ala Thr
            260                 265                 270

Gly Trp Arg Gly Leu Gln Cys Asn Glu Ala Cys Pro Tyr Gly His Tyr
        275                 280                 285

Gly Pro Asp Cys Lys Leu Arg Cys His Cys Thr Asn Glu Glu Met Cys
    290                 295                 300

Asp Arg Phe Gln Gly Cys Leu Cys Ser Gln Gly Trp Gln Gly Leu Gln
305                 310                 315                 320

Cys Glu Lys Glu Gly Arg Pro Arg Met Thr Pro Gln Ile Glu Asp Leu
                325                 330                 335

Pro Asp His Ile Glu Val Asn Ser Gly Lys Phe Asn Pro Ile Cys Lys
            340                 345                 350

Ala Ser Gly Trp Pro Leu Pro Thr Ser Glu Glu Met Thr Leu Val Lys
        355                 360                 365
```

-continued

Pro Asp Gly Thr Val Leu Gln Pro Asn Asp Phe Asn His Thr Asp His
    370                 375                 380

Phe Ser Val Ala Ile Phe Thr Val Asn Arg Ile Leu Pro Pro Asp Ser
385                 390                 395                 400

Gly Val Trp Val Cys Ser Val Asn Thr Val Ala Gly Met Val Glu Lys
                405                 410                 415

Pro Phe Asn Ile Ser Val Lys Val Leu Pro Glu Pro Leu His Ala Pro
            420                 425                 430

Asn Val Ile Asp Thr Gly His Asn Phe Ala Ile Ile Asn Ile Ser Ser
            435                 440                 445

Glu Pro Tyr Phe Gly Asp Gly Pro Ile Lys Ser Lys Lys Leu Phe Tyr
450                 455                 460

Lys Pro Val Asn Gln Ala Trp Lys Tyr Ile Gln Val Met Asn Glu Ile
465                 470                 475                 480

Val Thr Leu Asn Tyr Leu Glu Pro Arg Thr Asp Tyr Glu Leu Cys Val
                485                 490                 495

Gln Leu Val Arg Pro Gly Glu Gly Gly Glu His Pro Gly Pro Val
                500                 505                 510

Arg Arg Phe Thr Thr Ala Ser Ile Gly Leu Pro Pro Arg Gly Leu
            515                 520                 525

Ser Leu Leu Pro Lys Ser Gln Thr Ala Leu Asn Leu Thr Trp Gln Pro
530                 535                 540

Ile Phe Thr Ser Ser Glu Asp Glu Phe Tyr Val Glu Val Glu Arg Trp
545                 550                 555                 560

Ser Gln Gln Thr Arg Ser Asp Gln Gln Asn Ile Lys Val Pro Gly Asn
                565                 570                 575

Leu Thr Ser Val Leu Leu Asn Asn Leu Leu Pro Arg Glu Gln Tyr Ser
                580                 585                 590

Val Arg Ala Arg Val Asn Thr Lys Ala Gln Gly Glu Trp Ser Glu Glu
            595                 600                 605

Leu Arg Ala Trp Thr Leu Ser Asp Ile Leu Pro Pro Gln Pro Glu Asn
            610                 615                 620

Ile Lys Ile Thr Asn Ile Thr Asp Tyr Thr Ala Leu Val Ser Trp Thr
625                 630                 635                 640

Ile Val Asp Gly Tyr Ser Ile Ser Ser Ile Ile Arg Tyr Lys Val
                645                 650                 655

Gln Gly Lys Asn Glu Asp Gln His Ile Asp Val Lys Ile Lys Asn Ala
            660                 665                 670

Thr Ile Thr Gln Tyr Gln Leu Lys Gly Leu Glu Pro Glu Thr Thr Tyr
            675                 680                 685

His Val Asp Ile Phe Ala Glu Asn Asn Ile Gly Ser Ser Asn Pro Ala
    690                 695                 700

Phe Ser Gln Glu Ile Arg Thr Leu Pro Ala Pro Lys Asp Leu Gly Gly
705                 710                 715                 720

Gly Lys Gly Pro Gly Glu Pro Lys Ser Cys Asp Lys Thr His Thr Cys
                725                 730                 735

Pro Pro Cys Pro Ala Pro Glu Leu Leu Gly Gly Pro Ser Val Phe Leu
            740                 745                 750

Phe Pro Pro Lys Pro Lys Asp Thr Leu Met Ile Ser Arg Thr Pro Glu
            755                 760                 765

Val Thr Cys Val Val Val Asp Val Ser His Glu Asp Pro Glu Val Lys
770                 775                 780

Phe Asn Trp Tyr Val Asp Gly Val Glu Val His Asn Ala Lys Thr Lys

```
                785                 790                 795                 800
Pro Arg Glu Glu Gln Tyr Asn Ser Thr Tyr Arg Val Ser Val Leu
                    805                 810                 815

Thr Val Leu His Gln Asp Trp Leu Asn Gly Lys Glu Tyr Lys Cys Lys
                820                 825                 830

Val Ser Asn Lys Ala Leu Pro Ala Pro Ile Glu Lys Thr Ile Ser Lys
            835                 840                 845

Ala Lys Gly Gln Pro Arg Glu Pro Gln Val Tyr Thr Leu Pro Pro Ser
850                 855                 860

Arg Asp Glu Leu Thr Lys Asn Gln Val Ser Leu Thr Cys Leu Val Lys
865                 870                 875                 880

Gly Phe Tyr Pro Ser Asp Ile Ala Val Glu Trp Glu Ser Asn Gly Gln
                885                 890                 895

Pro Glu Asn Asn Tyr Lys Thr Thr Pro Pro Val Leu Asp Ser Asp Gly
                900                 905                 910

Ser Phe Phe Leu Tyr Ser Lys Leu Thr Val Asp Lys Ser Arg Trp Gln
            915                 920                 925

Gln Gly Asn Val Phe Ser Cys Ser Val Met His Glu Ala Leu His Asn
    930                 935                 940

His Tyr Thr Gln Lys Ser Leu Ser Leu Ser Pro Gly Lys
945                 950                 955

<210> SEQ ID NO 6
<211> LENGTH: 957
<212> TYPE: PRT
<213> ORGANISM: Artificial Sequence
<220> FEATURE:
<223> OTHER INFORMATION: Synthetic

<400> SEQUENCE: 6

Ala Met Asp Leu Ile Leu Ile Asn Ser Leu Pro Leu Val Ser Asp Ala
1               5                   10                  15

Glu Thr Ser Leu Thr Cys Ile Ala Ser Gly Trp His Pro His Glu Pro
                20                  25                  30

Ile Thr Ile Gly Arg Asp Phe Glu Ala Leu Met Asn Gln His Gln Asp
            35                  40                  45

Pro Leu Glu Val Thr Gln Asp Val Thr Arg Glu Trp Ala Lys Lys Val
    50                  55                  60

Val Trp Lys Arg Glu Lys Ala Ser Lys Ile Asn Gly Ala Tyr Phe Cys
65                  70                  75                  80

Glu Gly Arg Val Arg Gly Gln Ala Ile Arg Ile Arg Thr Met Lys Met
                85                  90                  95

Arg Gln Gln Ala Ser Phe Leu Pro Ala Thr Leu Thr Met Thr Val Asp
            100                 105                 110

Arg Gly Asp Asn Val Asn Ile Ser Phe Lys Lys Val Leu Ile Lys Glu
    115                 120                 125

Glu Asp Ala Val Ile Tyr Lys Asn Gly Ser Phe Ile His Ser Val Pro
130                 135                 140

Arg His Glu Val Pro Asp Ile Leu Glu Val His Leu Pro His Ala Gln
145                 150                 155                 160

Pro Gln Asp Ala Gly Val Tyr Ser Ala Arg Tyr Ile Gly Gly Asn Leu
                165                 170                 175

Phe Thr Ser Ala Phe Thr Arg Leu Ile Val Arg Arg Cys Glu Ala Gln
            180                 185                 190

Lys Trp Gly Pro Asp Cys Ser Arg Pro Cys Thr Thr Cys Lys Asn Asn
```

-continued

```
            195                 200                 205
Gly Val Cys His Glu Asp Thr Gly Glu Cys Ile Cys Pro Pro Gly Phe
            210                 215                 220

Met Gly Arg Thr Cys Glu Lys Ala Cys Glu Pro His Thr Phe Gly Arg
225                 230                 235                 240

Thr Cys Lys Glu Arg Cys Ser Gly Pro Glu Gly Cys Lys Ser Tyr Val
            245                 250                 255

Phe Cys Leu Pro Asp Pro Tyr Gly Cys Ser Cys Ala Thr Gly Trp Arg
            260                 265                 270

Gly Leu Gln Cys Asn Glu Ala Cys Pro Ser Gly Tyr Tyr Gly Pro Asp
            275                 280                 285

Cys Lys Leu Arg Cys His Cys Thr Asn Glu Glu Ile Cys Asp Arg Phe
            290                 295                 300

Gln Gly Cys Leu Cys Ser Gln Gly Trp Gln Gly Leu Gln Cys Glu Lys
305                 310                 315                 320

Glu Gly Arg Pro Arg Met Thr Pro Gln Ile Glu Asp Leu Pro Asp His
            325                 330                 335

Ile Glu Val Asn Ser Gly Lys Phe Asn Pro Ile Cys Lys Ala Ser Gly
            340                 345                 350

Trp Pro Leu Pro Thr Ser Glu Glu Met Thr Leu Val Lys Pro Asp Gly
            355                 360                 365

Thr Val Leu Gln Pro Asn Asp Phe Asn Tyr Thr Asp Arg Phe Ser Val
            370                 375                 380

Ala Ile Phe Thr Val Asn Arg Val Leu Pro Pro Asp Ser Gly Val Trp
385                 390                 395                 400

Val Cys Ser Val Asn Thr Val Ala Gly Met Val Glu Lys Pro Phe Asn
            405                 410                 415

Ile Ser Val Lys Val Leu Pro Glu Pro Leu His Ala Pro Asn Val Ile
            420                 425                 430

Asp Thr Gly His Asn Phe Ala Ile Ile Asn Ile Ser Ser Glu Pro Tyr
            435                 440                 445

Phe Gly Asp Gly Pro Ile Lys Ser Lys Lys Leu Phe Tyr Lys Pro Val
            450                 455                 460

Asn Gln Ala Trp Lys Tyr Ile Glu Val Thr Asn Glu Ile Phe Thr Leu
465                 470                 475                 480

Asn Tyr Leu Glu Pro Arg Thr Asp Tyr Glu Leu Cys Val Gln Leu Ala
            485                 490                 495

Arg Pro Gly Glu Gly Glu Gly His Pro Gly Pro Val Arg Arg Phe
            500                 505                 510

Thr Thr Ala Cys Ile Gly Leu Pro Pro Arg Gly Leu Ser Leu Leu
            515                 520                 525

Pro Lys Ser Gln Thr Ala Leu Asn Leu Thr Trp Gln Pro Ile Phe Thr
            530                 535                 540

Asn Ser Glu Asp Glu Phe Tyr Val Glu Val Glu Arg Arg Ser Leu Gln
545                 550                 555                 560

Thr Thr Ser Asp Gln Gln Asn Ile Lys Val Pro Gly Asn Leu Thr Ser
            565                 570                 575

Val Leu Leu Ser Asn Leu Val Pro Arg Glu Gln Tyr Thr Val Arg Ala
            580                 585                 590

Arg Val Asn Thr Lys Ala Gln Gly Glu Trp Ser Glu Leu Arg Ala
            595                 600                 605

Trp Thr Leu Ser Asp Ile Leu Pro Pro Gln Pro Glu Asn Ile Lys Ile
610                 615                 620
```

Ser Asn Ile Thr Asp Ser Thr Ala Met Val Ser Trp Thr Ile Val Asp
625                 630                 635                 640

Gly Tyr Ser Ile Ser Ser Ile Ile Ile Arg Tyr Lys Val Gln Gly Lys
            645                 650                 655

Asn Glu Asp Gln His Ile Asp Val Lys Ile Lys Asn Ala Thr Val Thr
        660                 665                 670

Gln Tyr Gln Leu Lys Gly Leu Glu Pro Glu Thr Thr Tyr His Val Asp
    675                 680                 685

Ile Phe Ala Glu Asn Asn Ile Gly Ser Ser Asn Pro Ala Phe Ser His
690                 695                 700

Glu Leu Arg Thr Leu Pro His Ser Pro Gly Ser Ala Asp Leu Gly Gly
705                 710                 715                 720

Gly Lys Gly Pro Gly Glu Pro Lys Ser Cys Asp Lys Thr His Thr Cys
            725                 730                 735

Pro Pro Cys Pro Ala Pro Glu Leu Leu Gly Gly Pro Ser Val Phe Leu
            740                 745                 750

Phe Pro Pro Lys Pro Lys Asp Thr Leu Met Ile Ser Arg Thr Pro Glu
        755                 760                 765

Val Thr Cys Val Val Val Asp Val Ser His Glu Asp Pro Glu Val Lys
770                 775                 780

Phe Asn Trp Tyr Val Asp Gly Val Glu Val His Asn Ala Lys Thr Lys
785                 790                 795                 800

Pro Arg Glu Glu Gln Tyr Asn Ser Thr Tyr Arg Val Val Ser Val Leu
            805                 810                 815

Thr Val Leu His Gln Asp Trp Leu Asn Gly Lys Glu Tyr Lys Cys Lys
            820                 825                 830

Val Ser Asn Lys Ala Leu Pro Ala Pro Ile Glu Lys Thr Ile Ser Lys
        835                 840                 845

Ala Lys Gly Gln Pro Arg Glu Pro Gln Val Tyr Thr Leu Pro Pro Ser
850                 855                 860

Arg Asp Glu Leu Thr Lys Asn Gln Val Ser Leu Thr Cys Leu Val Lys
865                 870                 875                 880

Gly Phe Tyr Pro Ser Asp Ile Ala Val Glu Trp Glu Ser Asn Gly Gln
            885                 890                 895

Pro Glu Asn Asn Tyr Lys Thr Thr Pro Pro Val Leu Asp Ser Asp Gly
            900                 905                 910

Ser Phe Phe Leu Tyr Ser Lys Leu Thr Val Asp Lys Ser Arg Trp Gln
        915                 920                 925

Gln Gly Asn Val Phe Ser Cys Ser Val Met His Glu Ala Leu His Asn
930                 935                 940

His Tyr Thr Gln Lys Ser Leu Ser Leu Ser Pro Gly Lys
945                 950                 955

<210> SEQ ID NO 7
<211> LENGTH: 321
<212> TYPE: PRT
<213> ORGANISM: Artificial Sequence
<220> FEATURE:
<223> OTHER INFORMATION: Synthetic

<400> SEQUENCE: 7

Met Asp Leu Ile Leu Ile Asn Ser Leu Pro Leu Val Ser Asp Ala Glu
1               5                   10                  15

Thr Ser Leu Thr Cys Ile Ala Ser Gly Trp Arg Pro His Glu Pro Ile
            20                  25                  30

Thr Ile Gly Arg Asp Phe Glu Ala Leu Met Asn Gln His Gln Asp Pro
            35                  40                  45

Leu Glu Val Thr Gln Asp Val Thr Arg Glu Trp Ala Lys Lys Val Val
        50                  55                  60

Trp Lys Arg Glu Lys Ala Ser Lys Ile Asn Gly Ala Tyr Phe Cys Glu
 65                  70                  75                  80

Gly Arg Val Arg Gly Glu Ala Ile Arg Ile Arg Thr Met Lys Met Arg
                85                  90                  95

Gln Gln Ala Ser Phe Leu Pro Ala Thr Leu Thr Met Thr Val Asp Lys
            100                 105                 110

Gly Asp Asn Val Asn Ile Ser Phe Lys Lys Val Leu Ile Lys Glu Glu
        115                 120                 125

Asp Ala Val Ile Tyr Lys Asn Gly Ser Phe Ile His Ser Val Pro Arg
130                 135                 140

His Glu Val Pro Asp Ile Leu Glu Val His Leu Pro His Ala Gln Pro
145                 150                 155                 160

Gln Asp Ala Gly Val Tyr Ser Ala Arg Tyr Ile Gly Gly Asn Leu Phe
                165                 170                 175

Thr Ser Ala Phe Thr Arg Leu Ile Val Arg Arg Cys Glu Ala Gln Lys
            180                 185                 190

Trp Gly Pro Glu Cys Asn His Leu Cys Thr Ala Cys Met Asn Asn Gly
        195                 200                 205

Val Cys His Glu Asp Thr Gly Glu Cys Ile Cys Pro Pro Gly Phe Met
    210                 215                 220

Gly Arg Thr Cys Glu Lys Ala Cys Glu Leu His Thr Phe Gly Arg Thr
225                 230                 235                 240

Cys Lys Glu Arg Cys Ser Gly Gln Glu Gly Cys Lys Ser Tyr Val Phe
                245                 250                 255

Cys Leu Pro Asp Pro Tyr Gly Cys Ser Cys Ala Thr Gly Trp Lys Gly
            260                 265                 270

Leu Gln Cys Asn Glu Ala Cys His Pro Gly Phe Tyr Gly Pro Asp Cys
        275                 280                 285

Lys Leu Arg Cys Ser Cys Asn Asn Gly Glu Met Cys Asp Arg Phe Gln
    290                 295                 300

Gly Cys Leu Cys Ser Pro Gly Trp Gln Gly Leu Gln Cys Glu Arg Glu
305                 310                 315                 320

Gly

<210> SEQ ID NO 8
<211> LENGTH: 226
<212> TYPE: PRT
<213> ORGANISM: Artificial Sequence
<220> FEATURE:
<223> OTHER INFORMATION: Synthetic

<400> SEQUENCE: 8

Met Ala Gln Ala Ser Phe Leu Pro Ala Thr Leu Thr Met Thr Val Asp
 1               5                  10                  15

Lys Gly Asp Asn Val Asn Ile Ser Phe Lys Lys Val Leu Ile Lys Glu
            20                  25                  30

Glu Asp Ala Val Ile Tyr Lys Asn Gly Ser Phe Ile His Ser Val Pro
        35                  40                  45

Arg His Glu Val Pro Asp Ile Leu Glu Val His Leu Pro His Ala Gln
    50                  55                  60

```
Pro Gln Asp Ala Gly Val Tyr Ser Ala Arg Tyr Ile Gly Gly Asn Leu
 65                  70                  75                  80

Phe Thr Ser Ala Phe Thr Arg Leu Ile Val Arg Arg Cys Glu Ala Gln
                 85                  90                  95

Lys Trp Gly Pro Glu Cys Asn His Leu Cys Thr Ala Cys Met Asn Asn
            100                 105                 110

Gly Val Cys His Glu Asp Thr Gly Glu Cys Ile Cys Pro Pro Gly Phe
        115                 120                 125

Met Gly Arg Thr Cys Glu Lys Ala Cys Glu Leu His Thr Phe Gly Arg
130                 135                 140

Thr Cys Lys Glu Arg Cys Ser Gly Gln Glu Gly Cys Lys Ser Tyr Val
145                 150                 155                 160

Phe Cys Leu Pro Asp Pro Tyr Gly Cys Ser Cys Ala Thr Gly Trp Lys
                165                 170                 175

Gly Leu Gln Cys Asn Glu Ala Cys His Pro Gly Phe Tyr Gly Pro Asp
            180                 185                 190

Cys Lys Leu Arg Cys Ser Cys Asn Asn Gly Glu Met Cys Asp Arg Phe
        195                 200                 205

Gln Gly Cys Leu Cys Ser Pro Gly Trp Gln Gly Leu Gln Cys Glu Arg
210                 215                 220

Glu Gly
225

<210> SEQ ID NO 9
<211> LENGTH: 140
<212> TYPE: PRT
<213> ORGANISM: Artificial Sequence
<220> FEATURE:
<223> OTHER INFORMATION: Synthetic

<400> SEQUENCE: 9

Met Ala Gly Ser Ala Arg Cys Glu Ala Gln Lys Trp Gly Pro Glu Cys
  1               5                  10                  15

Asn His Leu Cys Thr Ala Cys Met Asn Asn Gly Val Cys His Glu Asp
                 20                  25                  30

Thr Gly Glu Cys Ile Cys Pro Pro Gly Phe Met Gly Arg Thr Cys Glu
             35                  40                  45

Lys Ala Cys Glu Leu His Thr Phe Gly Arg Thr Cys Lys Glu Arg Cys
 50                  55                  60

Ser Gly Gln Glu Gly Cys Lys Ser Tyr Val Phe Cys Leu Pro Asp Pro
 65                  70                  75                  80

Tyr Gly Cys Ser Cys Ala Thr Gly Trp Lys Gly Leu Gln Cys Asn Glu
                 85                  90                  95

Ala Cys His Pro Gly Phe Tyr Gly Pro Asp Cys Lys Leu Arg Cys Ser
            100                 105                 110

Cys Asn Asn Gly Glu Met Cys Asp Arg Phe Gln Gly Cys Leu Cys Ser
        115                 120                 125

Pro Gly Trp Gln Gly Leu Gln Cys Glu Arg Glu Gly
    130                 135                 140

<210> SEQ ID NO 10
<211> LENGTH: 381
<212> TYPE: PRT
<213> ORGANISM: Artificial Sequence
<220> FEATURE:
<223> OTHER INFORMATION: Synthetic

<400> SEQUENCE: 10
```

```
Pro Lys Ile Val Asp Leu Pro Asp His Ile Glu Val Asn Ser Gly Lys
1               5                   10                  15

Phe Asn Pro Ile Cys Lys Ala Ser Gly Trp Pro Leu Pro Thr Asn Glu
                20                  25                  30

Glu Met Thr Leu Val Lys Pro Asp Gly Thr Val Leu His Pro Lys Asp
            35                  40                  45

Phe Asn His Thr Asp His Phe Ser Val Ala Ile Phe Thr Ile His Arg
        50                  55                  60

Ile Leu Pro Pro Asp Ser Gly Val Trp Val Cys Ser Val Asn Thr Val
65                  70                  75                  80

Ala Gly Met Val Glu Lys Pro Phe Asn Ile Ser Val Lys Val Leu Pro
                85                  90                  95

Lys Pro Leu Asn Ala Pro Asn Val Ile Asp Thr Gly His Asn Phe Ala
            100                 105                 110

Val Ile Asn Ile Ser Ser Glu Pro Tyr Phe Gly Asp Gly Pro Ile Lys
        115                 120                 125

Ser Lys Lys Leu Leu Tyr Lys Pro Val Asn His Tyr Glu Ala Trp Gln
130                 135                 140

His Ile Gln Val Thr Asn Glu Ile Val Thr Leu Asn Tyr Leu Glu Pro
145                 150                 155                 160

Arg Thr Glu Tyr Glu Leu Cys Val Gln Leu Val Arg Arg Gly Glu Gly
                165                 170                 175

Gly Glu Gly His Pro Gly Pro Val Arg Arg Phe Thr Thr Ala Ser Ile
            180                 185                 190

Gly Leu Pro Pro Arg Gly Leu Asn Leu Leu Pro Lys Ser Gln Thr
        195                 200                 205

Thr Leu Asn Leu Thr Trp Gln Pro Ile Phe Pro Ser Ser Glu Asp Asp
210                 215                 220

Phe Tyr Val Glu Val Glu Arg Arg Ser Val Gln Lys Ser Asp Gln Gln
225                 230                 235                 240

Asn Ile Lys Val Pro Gly Asn Leu Thr Ser Val Leu Leu Asn Asn Leu
                245                 250                 255

His Pro Arg Glu Gln Tyr Val Val Arg Ala Arg Val Asn Thr Lys Ala
            260                 265                 270

Gln Gly Glu Trp Ser Glu Asp Leu Thr Ala Trp Thr Leu Ser Asp Ile
        275                 280                 285

Leu Pro Pro Gln Pro Glu Asn Ile Lys Ile Ser Asn Ile Thr His Ser
290                 295                 300

Ser Ala Val Ile Ser Trp Thr Ile Leu Asp Gly Tyr Ser Ile Ser Ser
305                 310                 315                 320

Ile Thr Ile Arg Tyr Lys Val Gln Gly Lys Asn Glu Asp Gln His Val
                325                 330                 335

Asp Val Lys Ile Lys Asn Ala Thr Ile Thr Gln Tyr Gln Leu Lys Gly
            340                 345                 350

Leu Glu Pro Glu Thr Ala Tyr Gln Val Asp Ile Phe Ala Glu Asn Asn
        355                 360                 365

Ile Gly Ser Ser Asn Pro Ala Phe Ser His Glu Leu Val
370                 375                 380
```

<210> SEQ ID NO 11
<211> LENGTH: 286
<212> TYPE: PRT
<213> ORGANISM: Artificial Sequence
<220> FEATURE:

<223> OTHER INFORMATION: Synthetic

<400> SEQUENCE: 11

```
Pro Lys Pro Leu Asn Ala Pro Asn Val Ile Asp Thr Gly His Asn Phe
1               5                   10                  15

Ala Val Ile Asn Ile Ser Ser Glu Pro Tyr Phe Gly Asp Gly Pro Ile
            20                  25                  30

Lys Ser Lys Lys Leu Leu Tyr Lys Pro Val Asn His Tyr Glu Ala Trp
        35                  40                  45

Gln His Ile Gln Val Thr Asn Glu Ile Val Thr Leu Asn Tyr Leu Glu
    50                  55                  60

Pro Arg Thr Glu Tyr Glu Leu Cys Val Gln Leu Val Arg Arg Gly Glu
65                  70                  75                  80

Gly Gly Glu Gly His Pro Gly Pro Val Arg Arg Phe Thr Thr Ala Ser
                85                  90                  95

Ile Gly Leu Pro Pro Pro Arg Gly Leu Asn Leu Leu Pro Lys Ser Gln
            100                 105                 110

Thr Thr Leu Asn Leu Thr Trp Gln Pro Ile Phe Pro Ser Ser Glu Asp
            115                 120                 125

Asp Phe Tyr Val Glu Val Glu Arg Arg Ser Val Gln Lys Ser Asp Gln
130                 135                 140

Gln Asn Ile Lys Val Pro Gly Asn Leu Thr Ser Val Leu Leu Asn Asn
145                 150                 155                 160

Leu His Pro Arg Glu Gln Tyr Val Val Arg Ala Arg Val Asn Thr Lys
                165                 170                 175

Ala Gln Gly Glu Trp Ser Glu Asp Leu Thr Ala Trp Thr Leu Ser Asp
            180                 185                 190

Ile Leu Pro Pro Gln Pro Glu Asn Ile Lys Ile Ser Asn Ile Thr His
            195                 200                 205

Ser Ser Ala Val Ile Ser Trp Thr Ile Leu Asp Gly Tyr Ser Ile Ser
    210                 215                 220

Ser Ile Thr Ile Arg Tyr Lys Val Gln Gly Lys Asn Glu Asp Gln His
225                 230                 235                 240

Val Asp Val Lys Ile Lys Asn Ala Thr Ile Thr Gln Tyr Gln Leu Lys
                245                 250                 255

Gly Leu Glu Pro Glu Thr Ala Tyr Gln Val Asp Ile Phe Ala Glu Asn
            260                 265                 270

Asn Ile Gly Ser Ser Asn Pro Ala Phe Ser His Glu Leu Val
        275                 280                 285
```

<210> SEQ ID NO 12
<211> LENGTH: 995
<212> TYPE: PRT
<213> ORGANISM: Artificial Sequence
<220> FEATURE:
<223> OTHER INFORMATION: Synthetic

<400> SEQUENCE: 12

```
Met Val Trp Arg Val Pro Pro Phe Leu Leu Pro Ile Leu Phe Leu Ala
1               5                   10                  15

Ser His Val Gly Ala Ala Val Asp Leu Thr Leu Leu Ala Asn Leu Arg
            20                  25                  30

Leu Thr Asp Pro Gln Arg Phe Phe Leu Thr Cys Val Ser Gly Glu Ala
        35                  40                  45

Gly Ala Gly Arg Gly Ser Asp Ala Trp Gly Pro Pro Leu Leu Leu Glu
    50                  55                  60
```

```
Lys Asp Asp Arg Ile Val Arg Thr Pro Pro Gly Pro Pro Leu Arg Leu
 65                  70                  75                  80

Ala Arg Asn Gly Ser His Gln Val Thr Leu Arg Gly Phe Ser Lys Pro
                 85                  90                  95

Ser Asp Leu Val Gly Val Phe Ser Cys Val Gly Gly Ala Gly Ala Arg
                100                 105                 110

Arg Thr Arg Val Ile Tyr Val His Asn Ser Pro Gly Ala His Leu Leu
            115                 120                 125

Pro Asp Lys Val Thr His Thr Val Asn Lys Gly Asp Thr Ala Val Leu
            130                 135                 140

Ser Ala Arg Val His Lys Glu Lys Gln Thr Asp Val Ile Trp Lys Ser
145                 150                 155                 160

Asn Gly Ser Tyr Phe Tyr Thr Leu Asp Trp His Glu Ala Gln Asp Gly
                165                 170                 175

Arg Phe Leu Leu Gln Leu Pro Asn Val Gln Pro Pro Ser Ser Gly Ile
                180                 185                 190

Tyr Ser Ala Thr Tyr Leu Glu Ala Ser Pro Leu Gly Ser Ala Phe Phe
                195                 200                 205

Arg Leu Ile Val Arg Gly Cys Gly Ala Gly Arg Trp Gly Pro Gly Cys
                210                 215                 220

Thr Lys Glu Cys Pro Gly Cys Leu His Gly Gly Val Cys His Asp His
225                 230                 235                 240

Asp Gly Glu Cys Val Cys Pro Pro Gly Phe Thr Gly Thr Arg Cys Glu
                245                 250                 255

Gln Ala Cys Arg Glu Gly Arg Phe Gly Gln Ser Cys Gln Glu Gln Cys
                260                 265                 270

Pro Gly Ile Ser Gly Cys Arg Gly Leu Thr Phe Cys Leu Pro Asp Pro
                275                 280                 285

Tyr Gly Cys Ser Cys Gly Ser Gly Trp Arg Gly Ser Gln Cys Gln Glu
                290                 295                 300

Ala Cys Ala Pro Gly His Phe Gly Ala Asp Cys Arg Leu Gln Cys Gln
305                 310                 315                 320

Cys Gln Asn Gly Gly Thr Cys Asp Arg Phe Ser Gly Cys Val Cys Pro
                325                 330                 335

Ser Gly Trp His Gly Val His Cys Glu Lys Ser Asp Arg Ile Pro Gln
                340                 345                 350

Ile Leu Asn Met Ala Ser Glu Leu Glu Phe Asn Leu Glu Thr Met Pro
                355                 360                 365

Arg Ile Asn Cys Ala Ala Ala Gly Asn Pro Phe Pro Val Arg Gly Ser
                370                 375                 380

Ile Glu Leu Arg Lys Pro Asp Gly Thr Val Leu Leu Ser Thr Lys Ala
385                 390                 395                 400

Ile Val Glu Pro Glu Lys Thr Thr Ala Glu Phe Glu Val Pro Arg Leu
                405                 410                 415

Val Leu Ala Asp Ser Gly Phe Trp Glu Cys Arg Val Ser Thr Ser Gly
                420                 425                 430

Gly Gln Asp Ser Arg Arg Phe Lys Val Asn Val Lys Val Pro Pro Val
                435                 440                 445

Pro Leu Ala Ala Pro Arg Leu Leu Thr Lys Gln Ser Arg Gln Leu Val
                450                 455                 460

Val Ser Pro Leu Val Ser Phe Ser Gly Asp Gly Pro Ile Ser Thr Val
465                 470                 475                 480
```

```
Arg Leu His Tyr Arg Pro Gln Asp Ser Thr Met Asp Trp Ser Thr Ile
            485                 490                 495

Val Val Asp Pro Ser Glu Asn Val Thr Leu Met Asn Leu Arg Pro Lys
        500                 505                 510

Thr Gly Tyr Ser Val Arg Val Gln Leu Ser Arg Pro Gly Glu Gly Gly
            515                 520                 525

Glu Gly Ala Trp Gly Pro Pro Thr Leu Met Thr Thr Asp Cys Pro Glu
        530                 535                 540

Pro Leu Leu Gln Pro Trp Leu Glu Gly Trp His Val Glu Gly Thr Asp
545                 550                 555                 560

Arg Leu Arg Val Ser Trp Ser Leu Pro Leu Val Pro Gly Pro Leu Val
                565                 570                 575

Gly Asp Gly Phe Leu Leu Arg Leu Trp Asp Gly Thr Arg Gly Gln Glu
            580                 585                 590

Arg Arg Glu Asn Val Ser Ser Pro Gln Ala Arg Thr Ala Leu Leu Thr
        595                 600                 605

Gly Leu Thr Pro Gly Thr His Tyr Gln Leu Asp Val Gln Leu Tyr His
    610                 615                 620

Cys Thr Leu Leu Gly Pro Ala Ser Pro Pro Ala His Val Leu Leu Pro
625                 630                 635                 640

Pro Ser Gly Pro Pro Ala Pro Arg His Leu His Ala Gln Ala Leu Ser
                645                 650                 655

Asp Ser Glu Ile Gln Leu Thr Trp Lys His Pro Glu Ala Leu Pro Gly
            660                 665                 670

Pro Ile Ser Lys Tyr Val Val Glu Val Gln Val Ala Gly Gly Ala Gly
        675                 680                 685

Asp Pro Leu Trp Ile Asp Val Asp Arg Pro Glu Glu Thr Ser Thr Ile
    690                 695                 700

Ile Arg Gly Leu Asn Ala Ser Thr Arg Tyr Leu Phe Arg Met Arg Ala
705                 710                 715                 720

Ser Ile Gln Gly Leu Gly Asp Trp Ser Asn Thr Val Glu Glu Ser Thr
                725                 730                 735

Leu Gly Asn Gly Leu Gln Ala Glu Gly Pro Val Gln Glu Ser Arg Ala
            740                 745                 750

Ala Glu Glu Gly Leu Asp Gln Gln Gly Pro Gly Glu Pro Lys Ser Cys
        755                 760                 765

Asp Lys Thr His Thr Cys Pro Pro Cys Pro Ala Pro Glu Leu Leu Gly
    770                 775                 780

Gly Pro Ser Val Phe Leu Phe Pro Pro Lys Pro Lys Asp Thr Leu Met
785                 790                 795                 800

Ile Ser Arg Thr Pro Glu Val Thr Cys Val Val Val Asp Val Ser His
                805                 810                 815

Glu Asp Pro Glu Val Lys Phe Asn Trp Tyr Val Asp Gly Val Glu Val
            820                 825                 830

His Asn Ala Lys Thr Lys Pro Arg Glu Glu Gln Tyr Asn Ser Thr Tyr
        835                 840                 845

Arg Val Val Ser Val Leu Thr Val Leu His Gln Asp Trp Leu Asn Gly
    850                 855                 860

Lys Glu Tyr Lys Cys Lys Val Ser Asn Lys Ala Leu Pro Ala Pro Ile
865                 870                 875                 880

Glu Lys Thr Ile Ser Lys Ala Lys Gly Gln Pro Arg Glu Pro Gln Val
                885                 890                 895

Tyr Thr Leu Pro Pro Ser Arg Asp Glu Leu Thr Lys Asn Gln Val Ser
```

```
            900                 905                 910
Leu Thr Cys Leu Val Lys Gly Phe Tyr Pro Ser Asp Ile Ala Val Glu
            915                 920                 925

Trp Glu Ser Asn Gly Gln Pro Glu Asn Asn Tyr Lys Thr Thr Pro Pro
        930                 935                 940

Val Leu Asp Ser Asp Gly Ser Phe Phe Leu Tyr Ser Lys Leu Thr Val
945                 950                 955                 960

Asp Lys Ser Arg Trp Gln Gln Gly Asn Val Phe Ser Cys Ser Val Met
                965                 970                 975

His Glu Ala Leu His Asn His Tyr Thr Gln Lys Ser Leu Ser Leu Ser
            980                 985                 990

Pro Gly Lys
        995

<210> SEQ ID NO 13
<211> LENGTH: 657
<212> TYPE: PRT
<213> ORGANISM: Artificial Sequence
<220> FEATURE:
<223> OTHER INFORMATION: Synthetic

<400> SEQUENCE: 13

Arg Asp Cys Ala Glu Val Phe Lys Ser Gly His Thr Thr Asn Gly Ile
1               5                   10                  15

Tyr Thr Leu Thr Phe Pro Asn Ser Thr Glu Glu Ile Lys Ala Tyr Cys
            20                  25                  30

Asp Met Glu Ala Gly Gly Gly Gly Trp Thr Ile Ile Gln Arg Arg Glu
        35                  40                  45

Asp Gly Ser Val Asp Phe Gln Arg Thr Trp Lys Glu Tyr Lys Val Gly
    50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
        115                 120                 125

Ala Gly Lys Ile Ser Ser Ile Ser Gln Pro Gly Asn Asp Phe Ser Thr
    130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
```

```
            260                 265                 270
Tyr Val Asp Gly Val Glu Val His Asn Ala Lys Thr Lys Pro Arg Glu
            275                 280                 285
Glu Gln Tyr Asn Ser Thr Tyr Arg Val Val Ser Val Leu Thr Val Leu
            290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                    325                 330                 335
Gln Pro Arg Glu Pro Gln Val Tyr Thr Leu Pro Pro Ser Arg Asp Glu
                340                 345                 350
Leu Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
        370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                    405                 410                 415
Val Phe Ser Cys Ser Val Met His Glu Ala Leu His Asn His Tyr Thr
                420                 425                 430
Gln Lys Ser Leu Ser Leu Ser Pro Gly Lys Arg Asp Cys Ala Glu Val
            435                 440                 445
Phe Lys Ser Gly His Thr Thr Asn Gly Ile Tyr Thr Leu Thr Phe Pro
        450                 455                 460
Asn Ser Thr Glu Glu Ile Lys Ala Tyr Cys Asp Met Glu Ala Gly Gly
465                 470                 475                 480
Gly Gly Trp Thr Ile Ile Gln Arg Arg Glu Asp Gly Ser Val Asp Phe
                    485                 490                 495
Gln Arg Thr Trp Lys Glu Tyr Lys Val Gly Phe Gly Asn Pro Ser Gly
                500                 505                 510
Glu Tyr Trp Leu Gly Asn Glu Phe Val Ser Gln Leu Thr Asn Gln Gln
            515                 520                 525
Arg Tyr Val Leu Lys Ile His Leu Lys Asp Trp Glu Gly Asn Glu Ala
        530                 535                 540
Tyr Ser Leu Tyr Glu His Phe Tyr Leu Ser Ser Glu Glu Leu Asn Tyr
545                 550                 555                 560
Arg Ile His Leu Lys Gly Leu Thr Gly Thr Ala Gly Lys Ile Ser Ser
                    565                 570                 575
Ile Ser Gln Pro Gly Asn Asp Phe Ser Thr Lys Asp Gly Asp Asn Asp
                580                 585                 590
Lys Cys Ile Cys Lys Cys Ser Gln Met Leu Thr Gly Gly Trp Trp Phe
            595                 600                 605
Asp Ala Cys Gly Pro Ser Asn Leu Asn Gly Met Tyr Tyr Pro Gln Arg
        610                 615                 620
Gln Asn Thr Asn Lys Phe Asn Gly Ile Lys Trp Tyr Tyr Trp Lys Gly
625                 630                 635                 640
Ser Gly Tyr Ser Leu Lys Ala Thr Thr Met Met Ile Arg Pro Ala Asp
                    645                 650                 655
Phe

<210> SEQ ID NO 14
<211> LENGTH: 674
```

```
<212> TYPE: PRT
<213> ORGANISM: Artificial Sequence
<220> FEATURE:
<223> OTHER INFORMATION: Synthetic

<400> SEQUENCE: 14
```

Arg Asp Cys Ala Asp Val Tyr Gln Ala Gly Phe Asn Lys Ser Gly Ile
1               5                   10                  15

Tyr Thr Ile Tyr Ile Asn Asn Met Pro Glu Pro Lys Lys Val Phe Cys
            20                  25                  30

Asn Met Asp Val Asn Gly Gly Gly Trp Thr Val Ile Gln His Arg Glu
        35                  40                  45

Asp Gly Ser Leu Asp Phe Gln Arg Gly Trp Lys Glu Tyr Lys Met Gly
    50                  55                  60

Phe Gly Asn Pro Ser Gly Glu Tyr Trp Leu Gly Asn Glu Phe Ile Phe
65              70                  75                  80

Ala Ile Thr Ser Gln Arg Gln Tyr Met Leu Arg Ile Glu Leu Met Asp
            85                  90                  95

Trp Glu Gly Asn Arg Ala Tyr Ser Gln Tyr Asp Arg Phe His Ile Gly
        100                 105                 110

Asn Glu Lys Gln Asn Tyr Arg Leu Tyr Leu Lys Gly His Thr Gly Thr
    115                 120                 125

Ala Gly Lys Gln Ser Ser Leu Ile Leu His Gly Ala Asp Phe Ser Thr
130                 135                 140

Lys Asp Ala Asp Asn Asp Asn Cys Met Cys Lys Cys Ala Leu Met Leu
145                 150                 155                 160

Thr Gly Gly Trp Trp Phe Asp Ala Cys Gly Pro Ser Asn Leu Asn Gly
            165                 170                 175

Met Phe Tyr Thr Ala Gly Gln Asn His Gly Lys Leu Asn Gly Ile Lys
        180                 185                 190

Trp His Tyr Phe Lys Gly Pro Ser Tyr Ser Leu Arg Ser Thr Thr Met
    195                 200                 205

Met Ile Arg Pro Leu Asp Phe Gly Pro Gly Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Ala Pro Phe Arg Asp Cys Ala Asp
450                 455                 460

Val Tyr Gln Ala Gly Phe Asn Lys Ser Gly Ile Tyr Thr Ile Tyr Ile
465                 470                 475                 480

Asn Asn Met Pro Glu Pro Lys Lys Val Phe Cys Asn Met Asp Val Asn
            485                 490                 495

Gly Gly Gly Trp Thr Val Ile Gln His Arg Glu Asp Gly Ser Leu Asp
            500                 505                 510

Phe Gln Arg Gly Trp Lys Glu Tyr Lys Met Gly Phe Gly Asn Pro Ser
            515                 520                 525

Gly Glu Tyr Trp Leu Gly Asn Glu Phe Ile Phe Ala Ile Thr Ser Gln
            530                 535                 540

Arg Gln Tyr Met Leu Arg Ile Glu Leu Met Asp Trp Glu Gly Asn Arg
545                 550                 555                 560

Ala Tyr Ser Gln Tyr Asp Arg Phe His Ile Gly Asn Glu Lys Gln Asn
            565                 570                 575

Tyr Arg Leu Tyr Leu Lys Gly His Thr Gly Thr Ala Gly Lys Gln Ser
            580                 585                 590

Ser Leu Ile Leu His Gly Ala Asp Phe Ser Thr Lys Asp Ala Asp Asn
            595                 600                 605

Asp Asn Cys Met Cys Lys Cys Ala Leu Met Leu Thr Gly Gly Trp Trp
            610                 615                 620

Phe Asp Ala Cys Gly Pro Ser Asn Leu Asn Gly Met Phe Tyr Thr Ala
625                 630                 635                 640

Gly Gln Asn His Gly Lys Leu Asn Gly Ile Lys Trp His Tyr Phe Lys
            645                 650                 655

Gly Pro Ser Tyr Ser Leu Arg Ser Thr Thr Met Met Ile Arg Pro Leu
            660                 665                 670

Asp Phe

<210> SEQ ID NO 15
<211> LENGTH: 498
<212> TYPE: PRT
<213> ORGANISM: Homo sapiens

<400> SEQUENCE: 15

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
            50                  55                  60

Asn Ala Leu Gln Arg Asp Ala Pro His Val Glu Pro Asp Phe Ser Ser
65                  70                  75                  80
```

```
Gln Lys Leu Gln His Leu Glu His Val Met Glu Asn Tyr Thr Gln Trp
                 85                  90                  95
Leu Gln Lys Leu Glu Asn Tyr Ile Val Glu Asn Met Lys Ser Glu Met
            100                 105                 110
Ala Gln Ile Gln Gln Asn Ala Val Gln Asn His Thr Ala Thr Met Leu
        115                 120                 125
Glu Ile Gly Thr Ser Leu Leu Ser Gln Thr Ala Glu Gln Thr Arg Lys
    130                 135                 140
Leu Thr Asp Val Glu Thr Gln Val Leu Asn Gln Thr Ser Arg Leu Glu
145                 150                 155                 160
Ile Gln Leu Leu Glu Asn Ser Leu Ser Thr Tyr Lys Leu Glu Lys Gln
                165                 170                 175
Leu Leu Gln Gln Thr Asn Glu Ile Leu Lys Ile His Glu Lys Asn Ser
            180                 185                 190
Leu Leu Glu His Lys Ile Leu Glu Met Glu Gly Lys His Lys Glu Glu
        195                 200                 205
Leu Asp Thr Leu Lys Glu Glu Lys Glu Asn Leu Gln Gly Leu Val Thr
    210                 215                 220
Arg Gln Thr Tyr Ile Ile Gln Glu Leu Glu Lys Gln Leu Asn Arg Ala
225                 230                 235                 240
Thr Thr Asn Asn Ser Val Leu Gln Lys Gln Gln Leu Glu Leu Met Asp
                245                 250                 255
Thr Val His Asn Leu Val Asn Leu Cys Thr Lys Glu Gly Val Leu Leu
            260                 265                 270
Lys Gly Gly Lys Arg Glu Glu Lys Pro Phe Arg Asp Cys Ala Asp
        275                 280                 285
Val Tyr Gln Ala Gly Phe Asn Lys Ser Gly Ile Tyr Thr Ile Tyr Ile
    290                 295                 300
Asn Asn Met Pro Glu Pro Lys Lys Val Phe Cys Asn Met Asp Val Asn
305                 310                 315                 320
Gly Gly Gly Trp Thr Val Ile Gln His Arg Glu Asp Gly Ser Leu Asp
                325                 330                 335
Phe Gln Arg Gly Trp Lys Glu Tyr Lys Met Gly Phe Gly Asn Pro Ser
            340                 345                 350
Gly Glu Tyr Trp Leu Gly Asn Glu Phe Ile Phe Ala Ile Thr Ser Gln
        355                 360                 365
Arg Gln Tyr Met Leu Arg Ile Glu Leu Met Asp Trp Glu Gly Asn Arg
    370                 375                 380
Ala Tyr Ser Gln Tyr Asp Arg Phe His Ile Gly Asn Glu Lys Gln Asn
385                 390                 395                 400
Tyr Arg Leu Tyr Leu Lys Gly His Thr Gly Thr Ala Gly Lys Gln Ser
                405                 410                 415
Ser Leu Ile Leu His Gly Ala Asp Phe Ser Thr Lys Asp Ala Asp Asn
            420                 425                 430
Asp Asn Cys Met Cys Lys Cys Ala Leu Met Leu Thr Gly Gly Trp Trp
        435                 440                 445
Phe Asp Ala Cys Gly Pro Ser Asn Leu Asn Gly Met Phe Tyr Thr Ala
    450                 455                 460
Gly Gln Asn His Gly Lys Leu Asn Gly Ile Lys Trp His Tyr Phe Lys
465                 470                 475                 480
Gly Pro Ser Tyr Ser Leu Arg Ser Thr Thr Met Met Ile Arg Pro Leu
                485                 490                 495
Asp Phe
```

<210> SEQ ID NO 16
<211> LENGTH: 496
<212> TYPE: PRT
<213> ORGANISM: Homo sapiens

<400> SEQUENCE: 16

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
                180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
        290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
                340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
```

```
            370                 375                 380
Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
                420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
        450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 17
<211> LENGTH: 509
<212> TYPE: PRT
<213> ORGANISM: Mus musculus

<400> SEQUENCE: 17

Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
                20                  25                  30

Gln Ile His Gln Val Arg Arg Gly Gln Cys Ser Tyr Thr Phe Val Val
            35                  40                  45

Pro Glu Pro Asp Ile Cys Gln Leu Ala Pro Thr Ala Ala Pro Glu Ala
        50                  55                  60

Leu Gly Gly Ser Asn Ser Leu Gln Arg Asp Leu Pro Ala Ser Arg Leu
65                  70                  75                  80

His Leu Thr Asp Trp Arg Ala Gln Arg Ala Gln Arg Ala Gln Arg Val
                85                  90                  95

Ser Gln Leu Glu Lys Ile Leu Glu Asn Asn Thr Gln Trp Leu Leu Lys
                100                 105                 110

Leu Glu Gln Ser Ile Lys Val Asn Leu Arg Ser His Leu Val Gln Ala
            115                 120                 125

Gln Gln Asp Thr Ile Gln Asn Gln Thr Thr Thr Met Leu Ala Leu Gly
        130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                165                 170                 175

Leu Glu Asn Ser Leu Ser Thr Asn Lys Leu Glu Arg Gln Met Leu Met
            180                 185                 190

Gln Ser Arg Glu Leu Gln Arg Leu Gln Gly Arg Asn Arg Ala Leu Glu
        195                 200                 205

Thr Arg Leu Gln Ala Leu Glu Ala Gln His Gln Ala Gln Leu Asn Ser
210                 215                 220

Leu Gln Glu Lys Arg Glu Gln Leu His Ser Leu Leu Gly His Gln Thr
225                 230                 235                 240

Gly Thr Leu Ala Asn Leu Lys His Asn Leu His Ala Leu Ser Ser Asn
                245                 250                 255
```

Ser Ser Ser Leu Gln Gln Gln Gln Gln Leu Thr Glu Phe Val Gln
            260                 265                 270

Arg Leu Val Arg Ile Val Ala Gln Asp Gln His Pro Val Ser Leu Lys
        275                 280                 285

Thr Pro Lys Pro Val Phe Gln Asp Cys Ala Glu Ile Lys Arg Ser Gly
    290                 295                 300

Val Asn Thr Ser Gly Val Tyr Thr Ile Tyr Glu Thr Asn Met Thr Lys
305                 310                 315                 320

Pro Leu Lys Val Phe Cys Asp Met Glu Thr Asp Gly Gly Gly Trp Thr
                325                 330                 335

Leu Ile Gln His Arg Glu Asp Gly Ser Val Asn Phe Gln Arg Thr Trp
            340                 345                 350

Glu Glu Tyr Lys Glu Gly Phe Gly Asn Val Ala Arg Glu His Trp Leu
        355                 360                 365

Gly Asn Glu Ala Val His Arg Leu Thr Ser Arg Thr Ala Tyr Leu Leu
    370                 375                 380

Arg Val Glu Leu His Asp Trp Glu Gly Arg Gln Thr Ser Ile Gln Tyr
385                 390                 395                 400

Glu Asn Phe Gln Leu Gly Ser Glu Arg Gln Arg Tyr Ser Leu Ser Val
                405                 410                 415

Asn Asp Ser Ser Ser Ala Gly Arg Lys Asn Ser Leu Ala Pro Gln
            420                 425                 430

Gly Thr Lys Phe Ser Thr Lys Asp Met Asp Asn Asp Asn Cys Met Cys
    435                 440                 445

Lys Cys Ala Gln Met Leu Ser Gly Gly Trp Trp Phe Asp Ala Cys Gly
450                 455                 460

Leu Ser Asn Leu Asn Gly Ile Tyr Tyr Ser Val His Gln His Leu His
465                 470                 475                 480

Lys Ile Asn Gly Ile Arg Trp His Tyr Phe Arg Gly Pro Ser Tyr Ser
                485                 490                 495

Leu His Gly Thr Arg Met Met Leu Arg Pro Met Gly Ala
            500                 505

<210> SEQ ID NO 18
<211> LENGTH: 503
<212> TYPE: PRT
<213> ORGANISM: Homo sapiens

<400> SEQUENCE: 18

Met Leu Ser Gln Leu Ala Met Leu Gln Gly Ser Leu Leu Leu Val Val
1               5                   10                  15

Ala Thr Met Ser Val Ala Gln Gln Thr Arg Gln Glu Ala Asp Arg Gly
            20                  25                  30

Cys Glu Thr Leu Val Val Gln His Gly His Cys Ser Tyr Thr Phe Leu
        35                  40                  45

Leu Pro Lys Ser Glu Pro Cys Pro Pro Gly Pro Glu Val Ser Arg Asp
    50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
                85                  90                  95

Asn Thr Gln Trp Leu Lys Lys Leu Glu Arg Ala Ile Lys Thr Ile Leu
            100                 105                 110

Arg Ser Lys Leu Glu Gln Val Gln Gln Gln Met Ala Gln Asn Gln Thr
        115                 120                 125

```
Ala Pro Met Leu Glu Leu Gly Thr Ser Leu Leu Asn Gln Thr Thr Ala
        130                 135                 140
Gln Ile Arg Lys Leu Thr Asp Met Glu Ala Gln Leu Leu Asn Gln Thr
145                 150                 155                 160
Ser Arg Met Asp Ala Gln Met Pro Glu Thr Phe Leu Ser Thr Asn Lys
                165                 170                 175
Leu Glu Asn Gln Leu Leu Leu Gln Arg Gln Lys Leu Gln Gln Leu Gln
                180                 185                 190
Gly Gln Asn Ser Ala Leu Glu Lys Arg Leu Gln Ala Leu Glu Thr Lys
                195                 200                 205
Gln Gln Glu Glu Leu Ala Ser Ile Leu Ser Lys Lys Ala Lys Leu Leu
210                 215                 220
Asn Thr Leu Ser Arg Gln Ser Ala Ala Leu Thr Asn Ile Glu Arg Gly
225                 230                 235                 240
Leu Arg Gly Val Arg His Asn Ser Ser Leu Leu Gln Asp Gln Gln His
                245                 250                 255
Ser Leu Arg Gln Leu Leu Val Leu Leu Arg His Leu Val Gln Glu Arg
                260                 265                 270
Ala Asn Ala Ser Ala Pro Ala Phe Ile Met Ala Gly Glu Gln Val Phe
                275                 280                 285
Gln Asp Cys Ala Glu Ile Gln Arg Ser Gly Ala Ser Ala Ser Gly Val
290                 295                 300
Tyr Thr Ile Gln Val Ser Asn Ala Thr Lys Pro Arg Lys Val Phe Cys
305                 310                 315                 320
Asp Leu Gln Ser Ser Gly Gly Arg Trp Thr Leu Ile Gln Arg Arg Glu
                325                 330                 335
Asn Gly Thr Val Asn Phe Gln Arg Asn Trp Lys Asp Tyr Lys Gln Gly
                340                 345                 350
Phe Gly Asp Pro Ala Gly Glu His Trp Leu Gly Asn Glu Val Val His
                355                 360                 365
Gln Leu Thr Arg Arg Ala Ala Tyr Ser Leu Arg Val Glu Leu Gln Asp
                370                 375                 380
Trp Glu Gly His Glu Ala Tyr Ala Gln Tyr Glu His Phe His Leu Gly
385                 390                 395                 400
Ser Glu Asn Gln Leu Tyr Arg Leu Ser Val Val Gly Tyr Ser Gly Ser
                405                 410                 415
Ala Gly Arg Gln Ser Ser Leu Val Leu Gln Asn Thr Ser Phe Ser Thr
                420                 425                 430
Leu Asp Ser Asp Asn Asp His Cys Leu Cys Lys Cys Ala Gln Val Met
                435                 440                 445
Ser Gly Gly Trp Trp Phe Asp Ala Cys Gly Leu Ser Asn Leu Asn Gly
                450                 455                 460
Val Tyr Tyr His Ala Pro Asp Asn Lys Tyr Lys Met Asp Gly Ile Arg
465                 470                 475                 480
Trp His Tyr Phe Lys Gly Pro Ser Tyr Ser Leu Arg Ala Ser Arg Met
                485                 490                 495
Met Ile Arg Pro Leu Asp Ile
                500
```